US012753243B2

(12) United States Patent
Xu et al.

(10) Patent No.: US 12,753,243 B2
(45) Date of Patent: Oct. 6, 2026

(54) CD73-BINDING PROTEIN AND USE THEREOF

(71) Applicants: SHANGHAI HUAOTA BIOPHARMACEUTICAL CO., LTD., Shanghai (CN); HUABO BIOPHARM (SHANGHAI) CO., LTD., Shanghai (CN)

(72) Inventors: Jingen Xu, Shanghai (CN); Xiangyang Zhu, Shanghai (CN); Haijia Yu, Shanghai (CN); Xiaoyue Wei, Shanghai (CN); Lili Qu, Shanghai (CN); Xiaochen Ren, Shanghai (CN)

(73) Assignees: SHANGHAI HUAOTA BIOPHARMACEUTICAL CO., LTD., Shanghai (CN); HUABO BIOPHARM (SHANGHAI) CO., LTD., Shanghai (CN)

( * ) Notice: Subject to any disclaimer, the term of this patent is extended or adjusted under 35 U.S.C. 154(b) by 518 days.

(21) Appl. No.: 18/270,400

(22) PCT Filed: Jan. 12, 2022

(86) PCT No.: PCT/CN2022/071520
§ 371 (c)(1),
(2) Date: Jun. 29, 2023

(87) PCT Pub. No.: WO2022/152144
PCT Pub. Date: Jul. 21, 2022

(65) Prior Publication Data

US 2024/0067747 A1 Feb. 29, 2024

(30) Foreign Application Priority Data

Jan. 13, 2021 (CN) ......................... 202110045071.3

(51) Int. Cl.
*C07K 16/28* (2006.01)
*A61K 39/00* (2006.01)

(52) U.S. Cl.
CPC .... *C07K 16/2896* (2013.01); *A61K 2039/505* (2013.01); *C07K 2317/76* (2013.01); *C07K 2317/92* (2013.01)

(58) Field of Classification Search
CPC .................................................. C07K 16/2896
See application file for complete search history.

(56) References Cited

U.S. PATENT DOCUMENTS

2019/0062456 A1 2/2019 Lonberg et al.
2019/0352420 A1 11/2019 Hofmann et al.

FOREIGN PATENT DOCUMENTS

CA 3016187 A1 9/2017
CA 3145897 A1 2/2021
CN 110240654 A 9/2019
CN 110248668 A 9/2019
CN 110366563 A 10/2019
CN 111499747 A 8/2020
WO 2012019061 A2 2/2012
WO 2016081748 A2 5/2016
WO 2017152085 A1 9/2017
WO 2019230856 A1 12/2019
WO 2021017892 A1 2/2021
WO 2022122004 A1 6/2022

OTHER PUBLICATIONS

Rudikoff et al., Proc. Nat'l Acad. Sci. USA, 79:1979-83 (1982) (Year: 1982).*
Brown et al., J. Immunol., 156(9):3285-91 (1996) (Year: 1996).*
Marvin et. al., Biochemistry, 42(23):7077-7083 (2003) (Year: 2003).*
Chiu et al., Antibodies, 8(55):1-80. (2019) (Year: 2019).*
Stedman's Medical dictionary, 2012, p. 11760 (Year: 2012).*
HogenEsch et al. J. Controlled Release 2012; 164: 183-186 (Year: 2012).*
Tang et al. Cancer Letters 2016; 370:85-90 (Year: 2016).*
JPO, "Office Action for JP Application No. 2023-538013.", English Translation. Japan. Dec. 9, 2025. (Year: 2025).*
PCT/CN2022/071520 International Search Report dated Jul. 21, 2022.
Qi, Y., et al., CD73 (non-official translation: Research Progress on the Role and Regulatory Mechanism of Nucleotidase CD73 in Malignant Tumors), Carcinogenesis, Teratogenesis & Mutagenesis, vol. 32, No. 5, Sep. 2020.
Sudo, H., et al., Radiolabeled Human Monoclonal Antibody 067-213 has the Potential for Noninvasive Quantification of CD73 Expression, Intl J of Molecular Sciences, vol. 21, Mar. 26, 2020.
Terp, M.G., et al., Anti-Human CD73 Monoclonal Antibody Inhibits Metastasis Formation in Human Breast Cancer by Inducing Clustering and Internalization of CD73 Expressed on the Surface of Cancer Cells, The J of Immunology, vol. 191, Sep. 16, 2023.
EPO, "Supplementary European Search Report for EP Application No. 22739022.6", Munich, Germany, Nov. 4, 2024.
JPO, "Office Action for JP Application No. 2023-538013", Japan Dec. 9, 2025.
Stagg John et al: "Anti-CD73 antibody therapy inhibits breast tumor growth and metastasis", PNAS, Proceedings of the National Academy of Sciences, National Academy of Sciences, US, vol. 107, No. 4, Jan. 26, 2010 (Jan. 26, 2010), pp. 1547-1552.
Luca Antonioli et al: "Anti-CD73 in Cancer Immunotherapy: Awakening New Opportunities", HHS Public Access Author Manuscript, vol. 2, No. 2, Feb. 1, 2016.

(Continued)

*Primary Examiner* — Julie Wu
*Assistant Examiner* — Francesca Edgingtongiordano
(74) *Attorney, Agent, or Firm* — toutman pepper locke; Tim Tingkang Xia, Esq.

(57) ABSTRACT

Provided is an isolated antigen-binding protein, which can specifically bind to CD73 and includes at least one CDR in a heavy chain variable region VH, wherein the region VH includes an amino acid sequence as represented by SEQ ID NO: 49. Further provided are a preparation method for the isolated antigen-binding protein and the use thereof.

11 Claims, 3 Drawing Sheets

Specification includes a Sequence Listing.

(56) References Cited

OTHER PUBLICATIONS

Allard David et al: "Targeting the CD73-adenosine axis in immuno-oncology", Immunology Letters, vol. 205, May 24, 2018.
Allard et al., "Anti-CD73 therapy impairs tumor angiogenesis", Int. J. of Can. 2014, 1466-1473.

* cited by examiner

SEQUENCE LISTING

```
<160> NUMBER OF SEQ ID NOS: 55

<210> SEQ ID NO 1
<211> LENGTH: 14
<212> TYPE: PRT
<213> ORGANISM: Artificial Sequence
<220> FEATURE:
<223> OTHER INFORMATION: HCDR3

<400> SEQUENCE: 1

Ala Arg Tyr Tyr Gly Ser Asp Tyr Glu Trp Tyr Phe Asp Val
1               5                   10


<210> SEQ ID NO 2
<211> LENGTH: 8
<212> TYPE: PRT
<213> ORGANISM: Artificial Sequence
<220> FEATURE:
<223> OTHER INFORMATION: HCDR2

<400> SEQUENCE: 2

Ile His Pro Asn Ser Gly Ser Thr
1               5


<210> SEQ ID NO 3
<211> LENGTH: 8
<212> TYPE: PRT
<213> ORGANISM: Artificial Sequence
<220> FEATURE:
<223> OTHER INFORMATION: HCDR1

<400> SEQUENCE: 3

Gly Tyr Thr Phe Thr Ser Tyr Trp
1               5


<210> SEQ ID NO 4
<211> LENGTH: 9
<212> TYPE: PRT
<213> ORGANISM: Artificial Sequence
<220> FEATURE:
<223> OTHER INFORMATION: LCDR3

<400> SEQUENCE: 4

Leu Gln His Trp Asn Tyr Pro Tyr Thr
```

1 5

<210> SEQ ID NO 5
<211> LENGTH: 3
<212> TYPE: PRT
<213> ORGANISM: Artificial Sequence
<220> FEATURE:
<223> OTHER INFORMATION: LCDR2

<400> SEQUENCE: 5

Leu Ala Ser
1

<210> SEQ ID NO 6
<211> LENGTH: 6
<212> TYPE: PRT
<213> ORGANISM: Artificial Sequence
<220> FEATURE:
<223> OTHER INFORMATION: LCDR1

<400> SEQUENCE: 6

Gln Asn Val Arg Thr Ala
1 5

<210> SEQ ID NO 7
<211> LENGTH: 25
<212> TYPE: PRT
<213> ORGANISM: Artificial Sequence
<220> FEATURE:
<223> OTHER INFORMATION: 900567(124A9) H-FR1

<400> SEQUENCE: 7

Gln Val Gln Leu Gln Gln Pro Gly Ala Glu Leu Val Lys Pro Gly Ala
1 5 10 15

Ser Val Lys Leu Ser Cys Lys Ala Ser
20 25

<210> SEQ ID NO 8
<211> LENGTH: 17
<212> TYPE: PRT
<213> ORGANISM: Artificial Sequence
<220> FEATURE:
<223> OTHER INFORMATION: 900567(124A9) H-FR2

<400> SEQUENCE: 8

Ile His Trp Val Lys Gln Arg Pro Gly Gln Gly Leu Asp Trp Ile Gly
1 5 10 15

Met

<210> SEQ ID NO 9
<211> LENGTH: 38
<212> TYPE: PRT
<213> ORGANISM: Artificial Sequence
<220> FEATURE:
<223> OTHER INFORMATION: 900567(124A9) H-FR3

<400> SEQUENCE: 9

Tyr Tyr Asn Glu Lys Phe Lys Ser Lys Ala Thr Leu Thr Val Asp Lys
1 5 10 15

Ser Ser Ser Thr Ala Tyr Met Gln Leu Ser Ser Leu Thr Ser Glu Asp
20 25 30

Ser Ala Val Tyr Tyr Cys
35

<210> SEQ ID NO 10
<211> LENGTH: 11
<212> TYPE: PRT
<213> ORGANISM: Artificial Sequence
<220> FEATURE:
<223> OTHER INFORMATION: 900567(124A9) H-FR4

<400> SEQUENCE: 10

```
Trp Gly Thr Gly Thr Thr Val Thr Val Ser Ser
1               5                   10
```

<210> SEQ ID NO 11
<211> LENGTH: 26
<212> TYPE: PRT
<213> ORGANISM: Artificial Sequence
<220> FEATURE:
<223> OTHER INFORMATION: 900567(124A9) L-FR1

<400> SEQUENCE: 11

```
Asp Ile Val Met Thr Gln Ser Gln Lys Phe Met Ser Thr Ser Val Gly
1               5                   10                  15

Asp Arg Val Ser Ile Thr Cys Lys Ala Ser
            20                  25
```

<210> SEQ ID NO 12
<211> LENGTH: 17
<212> TYPE: PRT
<213> ORGANISM: Artificial Sequence
<220> FEATURE:
<223> OTHER INFORMATION: 900567(124A9) L-FR2

<400> SEQUENCE: 12

```
Val Val Trp Tyr Gln Gln Asn Pro Gly Gln Ser Pro Lys Ala Leu Ile
1               5                   10                  15

Tyr
```

<210> SEQ ID NO 13
<211> LENGTH: 36
<212> TYPE: PRT
<213> ORGANISM: Artificial Sequence
<220> FEATURE:
<223> OTHER INFORMATION: 900567(124A9) L-FR3

<400> SEQUENCE: 13

```
Asn Arg His Thr Gly Val Pro Asp Arg Phe Thr Gly Ser Gly Ser Gly
1               5                   10                  15

Thr Asp Phe Thr Leu Thr Ile Ser Asn Val His Ser Glu Asp Leu Ala
            20                  25                  30

Asp Tyr Phe Cys
        35
```

<210> SEQ ID NO 14
<211> LENGTH: 10
<212> TYPE: PRT
<213> ORGANISM: Artificial Sequence
<220> FEATURE:
<223> OTHER INFORMATION: 900567(124A9) L-FR4

<400> SEQUENCE: 14

```
Phe Gly Gly Gly Thr Lys Leu Glu Ile Lys
1               5                   10
```

<210> SEQ ID NO 15
<211> LENGTH: 25
<212> TYPE: PRT

<213> ORGANISM: Artificial Sequence
<220> FEATURE:
<223> OTHER INFORMATION: H-FR1 of 900725 900726

<400> SEQUENCE: 15

Gln Val Gln Leu Val Gln Ser Gly Ala Glu Val Lys Lys Pro Gly Ala
1               5                   10                  15

Ser Val Lys Leu Ser Cys Lys Ala Ser
            20                  25

<210> SEQ ID NO 16
<211> LENGTH: 17
<212> TYPE: PRT
<213> ORGANISM: Artificial Sequence
<220> FEATURE:
<223> OTHER INFORMATION: H-FR2 of 900725 900726 900727 900728

<400> SEQUENCE: 16

Ile His Trp Val Arg Gln Ala Pro Gly Gln Gly Leu Glu Trp Ile Gly
1               5                   10                  15

Met

<210> SEQ ID NO 17
<211> LENGTH: 38
<212> TYPE: PRT
<213> ORGANISM: Artificial Sequence
<220> FEATURE:
<223> OTHER INFORMATION: H-FR3 900725 900726

<400> SEQUENCE: 17

Tyr Tyr Asn Glu Lys Phe Lys Gly Arg Ala Thr Leu Thr Val Asp Lys
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35

<210> SEQ ID NO 18
<211> LENGTH: 11
<212> TYPE: PRT
<213> ORGANISM: Artificial Sequence
<220> FEATURE:
<223> OTHER INFORMATION: H-FR4 of 900725 900726 900727 900728

<400> SEQUENCE: 18

Trp Gly Gln Gly Thr Thr Val Thr Val Ser Ser
1               5                   10

<210> SEQ ID NO 19
<211> LENGTH: 26
<212> TYPE: PRT
<213> ORGANISM: Artificial Sequence
<220> FEATURE:
<223> OTHER INFORMATION: L-FR1 of 900725 900727

<400> SEQUENCE: 19

Asp Ile Gln Met Thr Gln Ser Pro Ser Ser Met Ser Ala Ser Val Gly
1               5                   10                  15

Asp Arg Val Thr Ile Thr Cys Lys Ala Ser
            20                  25

<210> SEQ ID NO 20
<211> LENGTH: 17
<212> TYPE: PRT

<213> ORGANISM: Artificial Sequence
<220> FEATURE:
<223> OTHER INFORMATION: L-FR2 of 900725 900726 900727 900728

<400> SEQUENCE: 20

Val Val Trp Tyr Gln Gln Lys Pro Gly Lys Ala Pro Lys Ala Leu Ile
1 5 10 15

Tyr

<210> SEQ ID NO 21
<211> LENGTH: 36
<212> TYPE: PRT
<213> ORGANISM: Artificial Sequence
<220> FEATURE:
<223> OTHER INFORMATION: L-FR3 of 900725 900727

<400> SEQUENCE: 21

Asn Arg His Thr Gly Val Pro Asp Arg Phe Ser Gly Ser Gly Ser Gly
1 5 10 15

Thr Asp Phe Thr Leu Thr Ile Ser Ser Leu Gln Pro Glu Asp Phe Ala
20 25 30

Thr Tyr Phe Cys
35

<210> SEQ ID NO 22
<211> LENGTH: 10
<212> TYPE: PRT
<213> ORGANISM: Artificial Sequence
<220> FEATURE:
<223> OTHER INFORMATION: L-FR4 of 900725 900726 900727 900728

<400> SEQUENCE: 22

Phe Gly Gln Gly Thr Lys Leu Glu Ile Lys
1 5 10

<210> SEQ ID NO 23
<211> LENGTH: 25
<212> TYPE: PRT
<213> ORGANISM: Artificial Sequence
<220> FEATURE:
<223> OTHER INFORMATION: H-FR1 of 900727 900728

<400> SEQUENCE: 23

Gln Val Gln Leu Val Gln Ser Gly Ala Glu Val Lys Lys Pro Gly Ala
1 5 10 15

Ser Val Lys Val Ser Cys Lys Ala Ser
20 25

<210> SEQ ID NO 24
<211> LENGTH: 38
<212> TYPE: PRT
<213> ORGANISM: Artificial Sequence
<220> FEATURE:
<223> OTHER INFORMATION: 900727 H-FR3

<400> SEQUENCE: 24

Tyr Tyr Ala Gln Lys Phe Gln Gly Arg Val Thr Ile Thr Val Asp Lys
1 5 10 15

Ser Thr Ser Thr Ala Tyr Met Glu Leu Ser Ser Leu Arg Ser Glu Asp
20 25 30

Thr Ala Val Tyr Tyr Cys
35

<210> SEQ ID NO 25
<211> LENGTH: 26
<212> TYPE: PRT
<213> ORGANISM: Artificial Sequence
<220> FEATURE:
<223> OTHER INFORMATION: L-FR1 of 900726 900728

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Lys Ala Ser
            20                  25
```

<210> SEQ ID NO 26
<211> LENGTH: 36
<212> TYPE: PRT
<213> ORGANISM: Artificial Sequence
<220> FEATURE:
<223> OTHER INFORMATION: L-FR3 of 900726 900728

<400> SEQUENCE: 26

```
Asn Arg His Thr Gly Val Pro Asp Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35
```

<210> SEQ ID NO 27
<211> LENGTH: 38
<212> TYPE: PRT
<213> ORGANISM: Artificial Sequence
<220> FEATURE:
<223> OTHER INFORMATION: 900728 H-FR3

<400> SEQUENCE: 27

```
Tyr Tyr Asn Glu Lys Phe Gln Gly Arg Val Thr Met Thr Val Asp Lys
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35
```

<210> SEQ ID NO 28
<211> LENGTH: 121
<212> TYPE: PRT
<213> ORGANISM: Artificial Sequence
<220> FEATURE:
<223> OTHER INFORMATION: 900567(124A9) VH

<400> SEQUENCE: 28

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile His Trp Val Lys Gln Arg Pro Gly Gln Gly Leu Asp Trp Ile
        35                  40                  45

Gly Met Ile His Pro Asn Ser Gly Ser Thr Tyr Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
```

```
                85                  90                  95

Ala Arg Tyr Tyr Gly Ser Asp Tyr Glu Trp Tyr Phe Asp Val Trp Gly
            100                 105                 110

Thr Gly Thr Thr Val Thr Val Ser Ser
        115                 120


<210> SEQ ID NO 29
<211> LENGTH: 107
<212> TYPE: PRT
<213> ORGANISM: Artificial Sequence
<220> FEATURE:
<223> OTHER INFORMATION: 900567(124A9) VL

<400> SEQUENCE: 29

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Ala
            20                  25                  30

Val Val Trp Tyr Gln Gln Asn Pro Gly Gln Ser Pro Lys Ala Leu Ile
        35                  40                  45

Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val His Ser
65                  70                  75                  80

Glu Asp Leu Ala Asp Tyr Phe Cys Leu Gln His Trp Asn Tyr Pro Tyr
                85                  90                  95

Thr Phe Gly Gly Gly Thr Lys Leu Glu Ile Lys
            100                 105


<210> SEQ ID NO 30
<211> LENGTH: 121
<212> TYPE: PRT
<213> ORGANISM: Artificial Sequence
<220> FEATURE:
<223> OTHER INFORMATION: VH of 900725 900726

<400> SEQUENCE: 30

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Ile
        35                  40                  45

Gly Met Ile His Pro Asn Ser Gly Ser Thr Tyr Tyr Asn Glu Lys Phe
    50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Gly Ser Asp Tyr Glu Trp Tyr Phe Asp Val Trp Gly
            100                 105                 110

Gln Gly Thr Thr Val Thr Val Ser Ser
        115                 120


<210> SEQ ID NO 31
<211> LENGTH: 107
<212> TYPE: PRT
<213> ORGANISM: Artificial Sequence
<220> FEATURE:
```

<223> OTHER INFORMATION: VL of 900725 900727

<400> SEQUENCE: 31

Asp Ile Gln Met Thr Gln Ser Pro Ser Ser Met Ser Ala Ser Val Gly
1 5 10 15

Asp Arg Val Thr Ile Thr Cys Lys Ala Ser Gln Asn Val Arg Thr Ala
20 25 30

Val Val Trp Tyr Gln Gln Lys Pro Gly Lys Ala Pro Lys Ala Leu Ile
35 40 45

Tyr Leu Ala Ser Asn Arg His Thr Gly Val Pro Asp Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Phe Cys Leu Gln His Trp Asn Tyr Pro Tyr
85 90 95

Thr Phe Gly Gln Gly Thr Lys Leu Glu Ile Lys
100 105

<210> SEQ ID NO 32
<211> LENGTH: 121
<212> TYPE: PRT
<213> ORGANISM: Artificial Sequence
<220> FEATURE:
<223> OTHER INFORMATION: 900727 VH

<400> SEQUENCE: 32

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Ile His Trp Val Arg Gln Ala Pro Gly Gln Gly Leu Glu Trp Ile
35 40 45

Gly Met Ile His Pro Asn Ser Gly Ser Thr Tyr Tyr Ala Gln Lys Phe
50 55 60

Gln Gly Arg Val Thr Ile Thr Val Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Tyr Tyr Gly Ser Asp Tyr Glu Trp Tyr Phe Asp Val Trp Gly
100 105 110

Gln Gly Thr Thr Val Thr Val Ser Ser
115 120

<210> SEQ ID NO 33
<211> LENGTH: 107
<212> TYPE: PRT
<213> ORGANISM: Artificial Sequence
<220> FEATURE:
<223> OTHER INFORMATION: VL of 900726 900728

<400> SEQUENCE: 33

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Val Arg Thr Ala
20 25 30

Val Val Trp Tyr Gln Gln Lys Pro Gly Lys Ala Pro Lys Ala Leu Ile
35 40 45

Tyr Leu Ala Ser Asn Arg His Thr Gly Val Pro Asp Arg Phe Ser Gly

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Trp Asn Tyr Pro Tyr
                85                  90                  95

Thr Phe Gly Gln Gly Thr Lys Leu Glu Ile Lys
            100                 105


<210> SEQ ID NO 34
<211> LENGTH: 121
<212> TYPE: PRT
<213> ORGANISM: Artificial Sequence
<220> FEATURE:
<223> OTHER INFORMATION: 900728 VH

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Ile
        35                  40                  45

Gly Met Ile His Pro Asn Ser Gly Ser Thr Tyr Tyr Asn Glu Lys Phe
    50                  55                  60

Gln Gly Arg Val Thr Met Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Gly Ser Asp Tyr Glu Trp Tyr Phe Asp Val Trp Gly
            100                 105                 110

Gln Gly Thr Thr Val Thr Val Ser Ser
        115                 120


<210> SEQ ID NO 35
<211> LENGTH: 121
<212> TYPE: PRT
<213> ORGANISM: Artificial Sequence
<220> FEATURE:
<223> OTHER INFORMATION: 900584 VH

<400> SEQUENCE: 35

Gln Val Gln Val Gln Gln Pro Gly Thr Glu Leu Val Lys Pro Gly Ala
1               5                   10                  15

Ser Val Lys Leu Ser Cys Lys Ala Ser Gly Tyr Thr Phe Thr Gly Tyr
            20                  25                  30

Trp Met His Trp Val Lys Gln Arg Pro Gly Gln Gly Leu Glu Trp Ile
        35                  40                  45

Gly Met Ile His Pro Asn Ser Gly Ser Thr Tyr Tyr Asn Glu Lys Phe
    50                  55                  60

Lys Ser Lys Ala Thr Leu Thr Val Asp Arg Ser Ser Ser Thr Ala Tyr
65                  70                  75                  80

Met Gln Leu Ser Ser Leu Ser Ser Glu Asp Ser Ala Val Tyr Tyr Cys
                85                  90                  95

Ala Arg Tyr Tyr Gly Thr Thr Tyr Glu Trp Tyr Phe Asp Val Trp Gly
            100                 105                 110

Thr Gly Thr Thr Val Thr Val Ser Ser
        115                 120
```

<210> SEQ ID NO 36
<211> LENGTH: 107
<212> TYPE: PRT
<213> ORGANISM: Artificial Sequence
<220> FEATURE:
<223> OTHER INFORMATION: 900584 VL

<400> SEQUENCE: 36

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Pro Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asp Leu Glu His
65                  70                  75                  80

Glu Asp Ile Ala Thr Tyr Phe Cys Gln Gln Gly Tyr Thr Leu Pro Phe
                85                  90                  95

Thr Phe Gly Gly Gly Thr Lys Leu Glu Ile Lys
            100                 105
```

<210> SEQ ID NO 37
<211> LENGTH: 329
<212> TYPE: PRT
<213> ORGANISM: Artificial Sequence
<220> FEATURE:
<223> OTHER INFORMATION: constant region of heavy chain

<400> SEQUENCE: 37

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 38
<211> LENGTH: 107
<212> TYPE: PRT
<213> ORGANISM: Artificial Sequence
<220> FEATURE:
<223> OTHER INFORMATION: constant region of light chain

<400> SEQUENCE: 38

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 39
<211> LENGTH: 446
<212> TYPE: PRT
<213> ORGANISM: Artificial Sequence
<220> FEATURE:
<223> OTHER INFORMATION: 900759(Oleclumab) heavy chain sequence

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Ala Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
```

```
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445


<210> SEQ ID NO 40
<211> LENGTH: 216
<212> TYPE: PRT
<213> ORGANISM: Artificial Sequence
<220> FEATURE:
<223> OTHER INFORMATION: 900759(Oleclumab) light chain sequence
```

<400> SEQUENCE: 40

```
Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
            20                  25                  30

Pro Val Asn Trp Tyr Gln Gln Leu Pro Gly Thr Ala Pro Lys Leu Leu
        35                  40                  45

Ile Tyr Leu Asp Asn Leu Arg Leu Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser His
                85                  90                  95

Pro Gly Trp Thr Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 41
<211> LENGTH: 25
<212> TYPE: PRT
<213> ORGANISM: Artificial Sequence
<220> FEATURE:
<223> OTHER INFORMATION: 900567(124A9) H-FR1; H-FR1 of 900725 900726; H-FR1 of 900727 900728
<220> FEATURE:
<221> NAME/KEY: misc_feature
<222> LOCATION: (5)..(5)
<223> OTHER INFORMATION: Xaa = Gln or Val
<220> FEATURE:
<221> NAME/KEY: misc_feature
<222> LOCATION: (7)..(7)
<223> OTHER INFORMATION: Xaa = Pro or Ser
<220> FEATURE:
<221> NAME/KEY: misc_feature
<222> LOCATION: (11)..(11)
<223> OTHER INFORMATION: Xaa = Leu or Val
<220> FEATURE:
<221> NAME/KEY: misc_feature
<222> LOCATION: (12)..(12)
<223> OTHER INFORMATION: Xaa = Lys or Val
<220> FEATURE:
<221> NAME/KEY: misc_feature
<222> LOCATION: (20)..(20)
<223> OTHER INFORMATION: Xaa = Leu or Val

<400> SEQUENCE: 41

```
Gln Val Gln Leu Xaa Gln Xaa Gly Ala Glu Xaa Xaa Lys Pro Gly Ala
1               5                   10                  15

Ser Val Lys Xaa Ser Cys Lys Ala Ser
```

20 25

<210> SEQ ID NO 42
<211> LENGTH: 17
<212> TYPE: PRT
<213> ORGANISM: Artificial Sequence
<220> FEATURE:
<223> OTHER INFORMATION: 900567(124A9) H-FR2; H-FR2 of 900725 900726 900727 900728
<220> FEATURE:
<221> NAME/KEY: misc_feature
<222> LOCATION: (5)..(5)
<223> OTHER INFORMATION: Xaa = Lys or Arg
<220> FEATURE:
<221> NAME/KEY: misc_feature
<222> LOCATION: (7)..(7)
<223> OTHER INFORMATION: Xaa = Ala or Arg
<220> FEATURE:
<221> NAME/KEY: misc_feature
<222> LOCATION: (13)..(13)
<223> OTHER INFORMATION: Xaa = Asp or Glu

<400> SEQUENCE: 42

Ile His Trp Val Xaa Gln Xaa Pro Gly Gln Gly Leu Xaa Trp Ile Gly
1 5 10 15

Met

<210> SEQ ID NO 43
<211> LENGTH: 38
<212> TYPE: PRT
<213> ORGANISM: Artificial Sequence
<220> FEATURE:
<223> OTHER INFORMATION: 900567(124A9) H-FR3; H-FR3 of 900725 900726; 900727 H-FR3; 900728 H-FR3
<220> FEATURE:
<221> NAME/KEY: misc_feature
<222> LOCATION: (3)..(3)
<223> OTHER INFORMATION: Xaa = Ala or Asn
<220> FEATURE:
<221> NAME/KEY: misc_feature
<222> LOCATION: (4)..(4)
<223> OTHER INFORMATION: Xaa = Glu or Gln
<220> FEATURE:
<221> NAME/KEY: misc_feature
<222> LOCATION: (7)..(7)
<223> OTHER INFORMATION: Xaa = Lys or Gln
<220> FEATURE:
<221> NAME/KEY: misc_feature
<222> LOCATION: (8)..(8)
<223> OTHER INFORMATION: Xaa = Gly or Ser
<220> FEATURE:
<221> NAME/KEY: misc_feature
<222> LOCATION: (9)..(9)
<223> OTHER INFORMATION: Xaa = Lys or Arg
<220> FEATURE:
<221> NAME/KEY: misc_feature
<222> LOCATION: (10)..(10)
<223> OTHER INFORMATION: Xaa = Ala or Val
<220> FEATURE:
<221> NAME/KEY: misc_feature
<222> LOCATION: (12)..(12)
<223> OTHER INFORMATION: Xaa = Ile or Leu or Met
<220> FEATURE:
<221> NAME/KEY: misc_feature
<222> LOCATION: (18)..(18)
<223> OTHER INFORMATION: Xaa = Ser or Thr
<220> FEATURE:
<221> NAME/KEY: misc_feature
<222> LOCATION: (24)..(24)
<223> OTHER INFORMATION: Xaa = Glu or Gln
<220> FEATURE:
<221> NAME/KEY: misc_feature
<222> LOCATION: (29)..(29)
<223> OTHER INFORMATION: Xaa = Arg or Thr
<220> FEATURE:

<221> NAME/KEY: misc_feature
<222> LOCATION: (33)..(33)
<223> OTHER INFORMATION: Xaa = Ser or Thr

<400> SEQUENCE: 43

Tyr Tyr Xaa Xaa Lys Phe Xaa Xaa Xaa Xaa Thr Xaa Thr Val Asp Lys
1 5 10 15

Ser Xaa Ser Thr Ala Tyr Met Xaa Leu Ser Ser Leu Xaa Ser Glu Asp
20 25 30

Xaa Ala Val Tyr Tyr Cys
35

<210> SEQ ID NO 44
<211> LENGTH: 11
<212> TYPE: PRT
<213> ORGANISM: Artificial Sequence
<220> FEATURE:
<223> OTHER INFORMATION: 900567(124A9) H-FR4; H-FR4 of 900725 900726 900727 900728
<220> FEATURE:
<221> NAME/KEY: misc_feature
<222> LOCATION: (3)..(3)
<223> OTHER INFORMATION: Xaa = Gln or Thr

<400> SEQUENCE: 44

Trp Gly Xaa Gly Thr Thr Val Thr Val Ser Ser
1 5 10

<210> SEQ ID NO 45
<211> LENGTH: 26
<212> TYPE: PRT
<213> ORGANISM: Artificial Sequence
<220> FEATURE:
<223> OTHER INFORMATION: 900567(124A9) L-FR1; L-FR1 of 900725 900727; L-FR1 of 900726 900728
<220> FEATURE:
<221> NAME/KEY: misc_feature
<222> LOCATION: (3)..(3)
<223> OTHER INFORMATION: Xaa = Gln or Val
<220> FEATURE:
<221> NAME/KEY: misc_feature
<222> LOCATION: (8)..(8)
<223> OTHER INFORMATION: Xaa = Pro or Gln
<220> FEATURE:
<221> NAME/KEY: misc_feature
<222> LOCATION: (9)..(9)
<223> OTHER INFORMATION: Xaa = Lys or Ser
<220> FEATURE:
<221> NAME/KEY: misc_feature
<222> LOCATION: (10)..(10)
<223> OTHER INFORMATION: Xaa = Phe or Ser
<220> FEATURE:
<221> NAME/KEY: misc_feature
<222> LOCATION: (11)..(11)
<223> OTHER INFORMATION: Xaa = Leu or Met
<220> FEATURE:
<221> NAME/KEY: misc_feature
<222> LOCATION: (13)..(13)
<223> OTHER INFORMATION: Xaa = Ala or Thr
<220> FEATURE:
<221> NAME/KEY: misc_feature
<222> LOCATION: (20)..(20)
<223> OTHER INFORMATION: Xaa = Ser or Thr

<400> SEQUENCE: 45

Asp Ile Xaa Met Thr Gln Ser Xaa Xaa Xaa Xaa Ser Xaa Ser Val Gly
1 5 10 15

Asp Arg Val Xaa Ile Thr Cys Lys Ala Ser
20 25

```
<210> SEQ ID NO 46
<211> LENGTH: 17
<212> TYPE: PRT
<213> ORGANISM: Artificial Sequence
<220> FEATURE:
<223> OTHER INFORMATION: 900567(124A9) L-FR2; L-FR2 of 900725 900726
      900727 900728
<220> FEATURE:
<221> NAME/KEY: misc_feature
<222> LOCATION: (7)..(7)
<223> OTHER INFORMATION: Xaa = Lys or Asn
<220> FEATURE:
<221> NAME/KEY: misc_feature
<222> LOCATION: (10)..(10)
<223> OTHER INFORMATION: Xaa = Lys or Gln
<220> FEATURE:
<221> NAME/KEY: misc_feature
<222> LOCATION: (11)..(11)
<223> OTHER INFORMATION: Xaa = Ala or Ser

<400> SEQUENCE: 46

Val Val Trp Tyr Gln Gln Xaa Pro Gly Xaa Xaa Pro Lys Ala Leu Ile
1               5                   10                  15

Tyr


<210> SEQ ID NO 47
<211> LENGTH: 36
<212> TYPE: PRT
<213> ORGANISM: Artificial Sequence
<220> FEATURE:
<223> OTHER INFORMATION: 900567(124A9) L-FR3;L-FR3 of 900725 900727;
      L-FR3 of 900726 900728
<220> FEATURE:
<221> NAME/KEY: misc_feature
<222> LOCATION: (11)..(11)
<223> OTHER INFORMATION: Xaa = Ser or Thr
<220> FEATURE:
<221> NAME/KEY: misc_feature
<222> LOCATION: (25)..(25)
<223> OTHER INFORMATION: Xaa = Asn or Ser
<220> FEATURE:
<221> NAME/KEY: misc_feature
<222> LOCATION: (26)..(26)
<223> OTHER INFORMATION: Xaa = Leu or Val
<220> FEATURE:
<221> NAME/KEY: misc_feature
<222> LOCATION: (27)..(27)
<223> OTHER INFORMATION: Xaa = His or Gln
<220> FEATURE:
<221> NAME/KEY: misc_feature
<222> LOCATION: (28)..(28)
<223> OTHER INFORMATION: Xaa = Pro or Ser
<220> FEATURE:
<221> NAME/KEY: misc_feature
<222> LOCATION: (31)..(31)
<223> OTHER INFORMATION: Xaa = Phe or Leu
<220> FEATURE:
<221> NAME/KEY: misc_feature
<222> LOCATION: (33)..(33)
<223> OTHER INFORMATION: Xaa = Asp or Thr
<220> FEATURE:
<221> NAME/KEY: misc_feature
<222> LOCATION: (35)..(35)
<223> OTHER INFORMATION: Xaa = Phe or Tyr

<400> SEQUENCE: 47

Asn Arg His Thr Gly Val Pro Asp Arg Phe Xaa Gly Ser Gly Ser Gly
1               5                   10                  15

Thr Asp Phe Thr Leu Thr Ile Ser Xaa Xaa Xaa Xaa Glu Asp Xaa Ala
            20                  25                  30

Xaa Tyr Xaa Cys
        35
```

<210> SEQ ID NO 48
<211> LENGTH: 10
<212> TYPE: PRT
<213> ORGANISM: Artificial Sequence
<220> FEATURE:
<223> OTHER INFORMATION: 900567(124A9) L-FR4; L-FR4 of 900725 900726
900727 900728
<220> FEATURE:
<221> NAME/KEY: misc_feature
<222> LOCATION: (3)..(3)
<223> OTHER INFORMATION: Xaa = Gly or Gln

<400> SEQUENCE: 48

Phe Gly Xaa Gly Thr Lys Leu Glu Ile Lys
1 5 10

<210> SEQ ID NO 49
<211> LENGTH: 121
<212> TYPE: PRT
<213> ORGANISM: Artificial Sequence
<220> FEATURE:
<223> OTHER INFORMATION: 900567(124A9) VH; VH of 900725 900726; 900727
VH; 900728 VH
<220> FEATURE:
<221> NAME/KEY: misc_feature
<222> LOCATION: (5)..(5)
<223> OTHER INFORMATION: Xaa = Gln or Val
<220> FEATURE:
<221> NAME/KEY: misc_feature
<222> LOCATION: (7)..(7)
<223> OTHER INFORMATION: Xaa = Pro or Ser
<220> FEATURE:
<221> NAME/KEY: misc_feature
<222> LOCATION: (11)..(11)
<223> OTHER INFORMATION: Xaa = Leu or Val
<220> FEATURE:
<221> NAME/KEY: misc_feature
<222> LOCATION: (12)..(12)
<223> OTHER INFORMATION: Xaa = Lys or Val
<220> FEATURE:
<221> NAME/KEY: misc_feature
<222> LOCATION: (20)..(20)
<223> OTHER INFORMATION: Xaa = Leu or Val
<220> FEATURE:
<221> NAME/KEY: misc_feature
<222> LOCATION: (38)..(38)
<223> OTHER INFORMATION: Xaa = Lys or Arg
<220> FEATURE:
<221> NAME/KEY: misc_feature
<222> LOCATION: (40)..(40)
<223> OTHER INFORMATION: Xaa = Ala or Arg
<220> FEATURE:
<221> NAME/KEY: misc_feature
<222> LOCATION: (46)..(46)
<223> OTHER INFORMATION: Xaa = Asp or Glu
<220> FEATURE:
<221> NAME/KEY: misc_feature
<222> LOCATION: (61)..(61)
<223> OTHER INFORMATION: Xaa = Ala or Asn
<220> FEATURE:
<221> NAME/KEY: misc_feature
<222> LOCATION: (62)..(62)
<223> OTHER INFORMATION: Xaa = Glu or Gln
<220> FEATURE:
<221> NAME/KEY: misc_feature
<222> LOCATION: (65)..(65)
<223> OTHER INFORMATION: Xaa = Lys or Gln
<220> FEATURE:
<221> NAME/KEY: misc_feature
<222> LOCATION: (66)..(66)
<223> OTHER INFORMATION: Xaa = Gly or Ser
<220> FEATURE:
<221> NAME/KEY: misc_feature
<222> LOCATION: (67)..(67)
<223> OTHER INFORMATION: Xaa = Lys or Arg
<220> FEATURE:

<221> NAME/KEY: misc_feature
<222> LOCATION: (68)..(68)
<223> OTHER INFORMATION: Xaa = Ala or Val
<220> FEATURE:
<221> NAME/KEY: misc_feature
<222> LOCATION: (70)..(70)
<223> OTHER INFORMATION: Xaa = Ile or Leu or Met
<220> FEATURE:
<221> NAME/KEY: misc_feature
<222> LOCATION: (76)..(76)
<223> OTHER INFORMATION: Xaa = Ser or Thr
<220> FEATURE:
<221> NAME/KEY: misc_feature
<222> LOCATION: (82)..(82)
<223> OTHER INFORMATION: Xaa = Glu or Gln
<220> FEATURE:
<221> NAME/KEY: misc_feature
<222> LOCATION: (87)..(87)
<223> OTHER INFORMATION: Xaa = Arg or Thr
<220> FEATURE:
<221> NAME/KEY: misc_feature
<222> LOCATION: (91)..(91)
<223> OTHER INFORMATION: Xaa = Ser or Thr
<220> FEATURE:
<221> NAME/KEY: misc_feature
<222> LOCATION: (113)..(113)
<223> OTHER INFORMATION: Xaa = Gln or Thr

<400> SEQUENCE: 49

```
Gln Val Gln Leu Xaa Gln Xaa Gly Ala Glu Xaa Xaa Lys Pro Gly Ala
1               5                   10                  15

Ser Val Lys Xaa Ser Cys Lys Ala Ser Gly Tyr Thr Phe Thr Ser Tyr
            20                  25                  30

Trp Ile His Trp Val Xaa Gln Xaa Pro Gly Gln Gly Leu Xaa Trp Ile
        35                  40                  45

Gly Met Ile His Pro Asn Ser Gly Ser Thr Tyr Tyr Xaa Xaa Lys Phe
    50                  55                  60

Xaa Xaa Xaa Xaa Thr Xaa Thr Val Asp Lys Ser Xaa Ser Thr Ala Tyr
65                  70                  75                  80

Met Xaa Leu Ser Ser Leu Xaa Ser Glu Asp Xaa Ala Val Tyr Tyr Cys
                85                  90                  95

Ala Arg Tyr Tyr Gly Ser Asp Tyr Glu Trp Tyr Phe Asp Val Trp Gly
            100                 105                 110

Xaa Gly Thr Thr Val Thr Val Ser Ser
        115                 120
```

<210> SEQ ID NO 50
<211> LENGTH: 107
<212> TYPE: PRT
<213> ORGANISM: Artificial Sequence
<220> FEATURE:
<223> OTHER INFORMATION: 900567(124A9)VL; VL of 900725 900727;VL of 900726 900728
<220> FEATURE:
<221> NAME/KEY: misc_feature
<222> LOCATION: (3)..(3)
<223> OTHER INFORMATION: Xaa = Gln or Val
<220> FEATURE:
<221> NAME/KEY: misc_feature
<222> LOCATION: (8)..(8)
<223> OTHER INFORMATION: Xaa = Pro or Gln
<220> FEATURE:
<221> NAME/KEY: misc_feature
<222> LOCATION: (9)..(9)
<223> OTHER INFORMATION: Xaa = Lys or Ser
<220> FEATURE:
<221> NAME/KEY: misc_feature
<222> LOCATION: (10)..(10)
<223> OTHER INFORMATION: Xaa = Phe or Ser
<220> FEATURE:

<221> NAME/KEY: misc_feature
<222> LOCATION: (11)..(11)
<223> OTHER INFORMATION: Xaa = Leu or Met
<220> FEATURE:
<221> NAME/KEY: misc_feature
<222> LOCATION: (13)..(13)
<223> OTHER INFORMATION: Xaa = Ala or Thr
<220> FEATURE:
<221> NAME/KEY: misc_feature
<222> LOCATION: (20)..(20)
<223> OTHER INFORMATION: Xaa = Ser or Thr
<220> FEATURE:
<221> NAME/KEY: misc_feature
<222> LOCATION: (39)..(39)
<223> OTHER INFORMATION: Xaa = Lys or Asn
<220> FEATURE:
<221> NAME/KEY: misc_feature
<222> LOCATION: (42)..(42)
<223> OTHER INFORMATION: Xaa = Lys or Gln
<220> FEATURE:
<221> NAME/KEY: misc_feature
<222> LOCATION: (43)..(43)
<223> OTHER INFORMATION: Xaa = Ala or Ser
<220> FEATURE:
<221> NAME/KEY: misc_feature
<222> LOCATION: (63)..(63)
<223> OTHER INFORMATION: Xaa = Ser or Thr
<220> FEATURE:
<221> NAME/KEY: misc_feature
<222> LOCATION: (77)..(77)
<223> OTHER INFORMATION: Xaa = Asn or Ser
<220> FEATURE:
<221> NAME/KEY: misc_feature
<222> LOCATION: (78)..(78)
<223> OTHER INFORMATION: Xaa = Leu or Val
<220> FEATURE:
<221> NAME/KEY: misc_feature
<222> LOCATION: (79)..(79)
<223> OTHER INFORMATION: Xaa = His or Gln
<220> FEATURE:
<221> NAME/KEY: misc_feature
<222> LOCATION: (80)..(80)
<223> OTHER INFORMATION: Xaa = Pro or Ser
<220> FEATURE:
<221> NAME/KEY: misc_feature
<222> LOCATION: (83)..(83)
<223> OTHER INFORMATION: Xaa = Phe or Leu
<220> FEATURE:
<221> NAME/KEY: misc_feature
<222> LOCATION: (85)..(85)
<223> OTHER INFORMATION: Xaa = Asp or Thr
<220> FEATURE:
<221> NAME/KEY: misc_feature
<222> LOCATION: (87)..(87)
<223> OTHER INFORMATION: Xaa = Phe or Tyr
<220> FEATURE:
<221> NAME/KEY: misc_feature
<222> LOCATION: (100)..(100)
<223> OTHER INFORMATION: Xaa = Gly or Gln

<400> SEQUENCE: 50

```
Asp Ile Xaa Met Thr Gln Ser Xaa Xaa Xaa Xaa Ser Xaa Ser Val Gly
1               5                   10                  15

Asp Arg Val Xaa Ile Thr Cys Lys Ala Ser Gln Asn Val Arg Thr Ala
            20                  25                  30

Val Val Trp Tyr Gln Gln Xaa Pro Gly Xaa Xaa Pro Lys Ala Leu Ile
        35                  40                  45

Tyr Leu Ala Ser Asn Arg His Thr Gly Val Pro Asp Arg Phe Xaa Gly
    50                  55                  60

Ser Gly Ser Gly Thr Asp Phe Thr Leu Thr Ile Ser Xaa Xaa Xaa Xaa
65                  70                  75                  80

Glu Asp Xaa Ala Xaa Tyr Xaa Cys Leu Gln His Trp Asn Tyr Pro Tyr
                85                  90                  95
```

```
Thr Phe Gly Xaa Gly Thr Lys Leu Glu Ile Lys
            100                 105


<210> SEQ ID NO 51
<211> LENGTH: 450
<212> TYPE: PRT
<213> ORGANISM: Artificial Sequence
<220> FEATURE:
<223> OTHER INFORMATION: 900201 heavy chain

<400> SEQUENCE: 51

Gln Ile Gln Leu Val Gln Ser Gly Pro Glu Leu Lys Lys Pro Gly Glu
1               5                   10                  15

Thr Val Lys Ile Ser Cys Lys Thr Ser Gly Tyr Thr Phe Thr Asn Tyr
            20                  25                  30

Gly Met Asn Trp Val Lys Gln Ala Pro Gly Lys Gly Leu Lys Trp Val
        35                  40                  45

Gly Trp Ile Asn Thr Tyr Thr Gly Glu Pro Lys Tyr Ala Asp Asp Phe
    50                  55                  60

Lys Gly Arg Phe Ala Phe Ser Val Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Ile Tyr Asp Gly Tyr His Trp Tyr Phe Asp Val Trp Gly
            100                 105                 110

Ala Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350
```

```
Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 52
<211> LENGTH: 219
<212> TYPE: PRT
<213> ORGANISM: Artificial Sequence
<220> FEATURE:
<223> OTHER INFORMATION: 900201 light chain

<400> SEQUENCE: 52

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Ile Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Thr Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 53
<211> LENGTH: 447
<212> TYPE: PRT
<213> ORGANISM: Artificial Sequence
```

<220> FEATURE:
<223> OTHER INFORMATION: Oleclumab heavy chain

<400> SEQUENCE: 53

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Ala Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 54
<211> LENGTH: 215
<212> TYPE: PRT
<213> ORGANISM: Artificial Sequence
<220> FEATURE:
<223> OTHER INFORMATION: Oleclumab light chain

<400> SEQUENCE: 54

Gln Ser Val Leu Thr Gln Pro Pro Ser Ala Ser Gly Thr Pro Gly Gln
1 5 10 15

Arg Val Thr Ile Ser Cys Ser Gly Ser Leu Ser Asn Ile Gly Arg Asn
20 25 30

Pro Val Asn Trp Tyr Gln Gln Leu Pro Gly Thr Ala Pro Lys Leu Leu
35 40 45

Ile Tyr Leu Asp Asn Leu Arg Leu Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Thr Trp Asp Asp Ser His
85 90 95

Pro Gly Trp Thr Phe Gly Gly Gly Thr Lys Leu Thr Val Leu Gln Pro
100 105 110

Lys Ala Ala Pro Ser Val Thr Leu Phe Pro Pro Ser Ser Glu Glu Leu
115 120 125

Gln Ala Asn Lys Ala Thr Leu Val Cys Leu Ile Ser Asp Phe Tyr Pro
130 135 140

Gly Ala Val Thr Val Ala Trp Lys Ala Asp Ser Ser Pro Val Lys Ala
145 150 155 160

Gly Val Glu Thr Thr Thr Pro Ser Lys Gln Ser Asn Asn Lys Tyr Ala
165 170 175

Ala Ser Ser Tyr Leu Ser Leu Thr Pro Glu Gln Trp Lys Ser His Arg
180 185 190

Ser Tyr Ser Cys Gln Val Thr His Glu Gly Ser Thr Val Glu Lys Thr
195 200 205

Val Ala Pro Thr Glu Cys Ser
210 215

<210> SEQ ID NO 55
<211> LENGTH: 450
<212> TYPE: PRT
<213> ORGANISM: Artificial Sequence
<220> FEATURE:
<223> OTHER INFORMATION: 900543 HC

<400> SEQUENCE: 55

Gln Ile Gln Leu Val Gln Ser Gly Pro Glu Leu Lys Lys Pro Gly Glu
1 5 10 15

Thr Val Lys Ile Ser Cys Lys Thr Ser Gly Tyr Thr Phe Thr Asn Tyr
20 25 30

Gly Met Asn Trp Val Lys Gln Ala Pro Gly Lys Gly Leu Lys Trp Val

-continued

```
        35                  40                  45

Gly Trp Ile Asn Thr Tyr Thr Gly Glu Pro Lys Tyr Ala Asp Asp Phe
    50                  55                  60

Lys Gly Arg Phe Ala Phe Ser Val Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Ile Tyr Asp Gly Tyr His Trp Tyr Phe Asp Val Trp Gly
            100                 105                 110

Ala Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

-continued

```
His Glu Ala Leu His Asn His Tyr Thr Gln Lys Ser Leu Ser Leu Ser
        435                 440                 445

Pro Gly
    450
```

CD73-BINDING PROTEIN AND USE THEREOF

CROSS REFERENCE TO RELATED APPLICATIONS

This application is a National Stage Application and claims priority under 35 U.S.C. § 371 to Patent Cooperation Treaty application PCT/CN2022/071520, filed Jan. 12, 2022, which claims the benefit of China Patent Application 202110045071.3 filed Jan. 13, 2021. Priority is claimed to these applications and the disclosure of these prior applications is considered part of the disclosure of this application and to the extent allowed the entire contents of the aforementioned applications are incorporated herein.

SEQUENCE LISTING

This application incorporates by reference in its entirety the Sequence Listing entitled "2023 Jun. 28 262790-528578_ST25.txt", is 54,644 bytes in size and was created on Jun. 28, 2023, and filed electronically herewith.

FIELD OF THE INVENTION

This application relates to the field of biomedicine, and in particular to an antigen-binding protein of CD73 and its application.

BACKGROUND OF THE INVENTION

CD73 is an ecto-5'-nucleotidase (NT5E) with a molecular weight of about 70 Kd. It is anchored to the cell surface by glycosyl-phosphatidylinositol (GPI) and exists mainly in the form of dimers. Under normal physiological conditions, the CD73 can be expressed in various tissues or organs, such as liver, large intestine, kidney, spleen, lung, ovary, lymph nodes and other tissues.

A large number of preclinical studies have shown that CD73 is abnormally highly expressed on the surface of various tumor cells, and clinical data show that high CD73 expression is closely related to the poor prognosis of tumor patients. Therefore, CD73 can be used as a potential target for clinical treatment and prognosis of various tumors.

However, there is no antibody or small-molecule drug against human CD73 on the market at present, and it is urgent to develop more drugs targeting tumor CD73, so as to provide new ideas and prospects for the treatment of cancers with abnormal expression of CD73.

SUMMARY OF THE INVENTION

This application provides an isolated antigen-binding protein having one or more of the following properties: 1) capable of specifically binding to a CD73 or a functionally active fragment thereof; 2) capable of specifically binds to a human CD73 and/or a monkey CD73; 3) capable of inhibiting the enzymatic activity of the CD73; 4) capable of inducing endocytosis of the CD73 on a cell surface; 5) has Tm and/or Tagg values higher than 65° C.; 6) has no or weak non-specific electrostatic binding; and 7) capable of inhibiting tumor growth. This application further provides nucleic acid molecules encoding the isolated antigen-binding protein, expression vectors, host cells and methods for preparing the isolated antigen-binding protein. The isolated antigen-binding protein of this application can be used in the prevention and/or treatment of diseases and/or disorders, such as tumors.

In one aspect, this application provides an isolated antigen-binding protein comprising at least one CDR in a heavy-chain variable region VH, the VH comprising an amino acid sequence as set forth in SEQ ID NO: 49.

In some embodiments, the isolated antigen-binding protein comprises an HCDR3, and the HCDR3 comprises an amino acid sequence as set forth in SEQ ID NO: 1.

In some embodiments, the isolated antigen-binding protein comprises an HCDR2, and the HCDR2 comprises an amino acid sequence as set forth in SEQ ID NO: 2.

In some embodiments, the isolated antigen-binding protein comprises an HCDR1, and the HCDR1 comprises an amino acid sequence as set forth in SEQ ID NO: 3.

In some embodiments, the isolated antigen-binding protein comprises at least one CDR in a light-chain variable region VL, the VL comprises an amino acid sequence as set forth in SEQ ID NO: 50.

In some embodiments, the isolated antigen-binding protein comprises an LCDR3, and the LCDR3 comprises an amino acid sequence as set forth in SEQ ID NO: 4.

In some embodiments, the isolated antigen-binding protein comprises an LCDR2, and the LCDR2 comprises an amino acid sequence as set forth in SEQ ID NO: 5.

In some embodiments, the isolated antigen-binding protein comprises an LCDR1, and the LCDR1 comprises an amino acid sequence as set forth in SEQ ID NO: 6.

In some embodiments, the isolated antigen-binding protein comprises an H-FR1, a C terminal of the H-FR1 is directly or indirectly linked to an N terminal of the HCDR1, and the H-FR1 comprises an amino acid sequence as set forth in SEQ ID NO: 41.

In some embodiments, the H-FR1 of the isolated antigen-binding protein comprises an amino acid sequence as set forth in any one of SEQ ID NO: 7, SEQ ID NO: 15, and SEQ ID NO: 23.

In some embodiments, the isolated antigen-binding protein comprises an H-FR2, and the H-FR2 is located between the HCDR1 and the HCDR2 and comprises an amino acid sequence as set forth in SEQ ID NO: 42.

In some embodiments, the H-FR2 of the isolated antigen-binding protein comprises an amino acid sequence as set forth in SEQ ID NO: 8 or SEQ ID NO: 16.

In some embodiments, the isolated antigen-binding protein comprises an H-FR3, and the H-FR3 is located between the HCDR2 and the HCDR3 and comprises an amino acid sequence as set forth in SEQ ID NO: 43.

In some embodiments, the H-FR3 of the isolated antigen-binding protein comprises an amino acid sequence as set forth in any one of SEQ ID NO: 9, SEQ ID NO: 17, SEQ ID NO: 24, and SEQ ID NO: 27.

In some embodiments, the isolated antigen-binding protein comprises an H-FR4, an N terminal of the H-FR4 is linked to a C terminal of the HCDR3, and the H-FR4 comprises an amino acid sequence as set forth in SEQ ID NO: 44.

In some embodiments, the H-FR4 of the isolated antigen-binding protein comprises an amino acid sequence as set forth in SEQ ID NO: 10 or SEQ ID NO: 18.

In some embodiments, the isolated antigen-binding protein comprises an L-FR1, a C terminal of the L-FR1 is directly or indirectly linked to an N terminal of the LCDR1, and the L-FR1 comprises an amino acid sequence as set forth in SEQ ID NO: 45.

In some embodiments, the L-FR1 of the isolated antigen-binding protein comprises an amino acid sequence as set forth in any one of SEQ ID NO: 11, SEQ ID NO: 19, and SEQ ID NO: 25.

In some embodiments, the isolated antigen-binding protein comprises an L-FR2, and the L-FR2 is located between the LCDR1 and the LCDR2 and comprises an amino acid sequence as set forth in SEQ ID NO: 46.

In some embodiments, the L-FR2 of the isolated antigen-binding protein comprises an amino acid sequence as set forth in SEQ ID NO: 12 or SEQ ID NO: 20.

In some embodiments, the isolated antigen-binding protein comprises an L-FR3, and the L-FR3 is located between the LCDR2 and the LCDR3 and comprises an amino acid sequence as set forth in SEQ ID NO: 47.

In some embodiments, the L-FR3 of the isolated antigen-binding protein comprises an amino acid sequence as set forth in any one of SEQ ID NO: 13, SEQ ID NO: 21, and SEQ ID NO: 26.

In some embodiments, the isolated antigen-binding protein comprises an L-FR4, an N terminal of the L-FR4 is linked to a C terminal of the LCDR3, and the L-FR4 comprises an amino acid sequence as set forth in SEQ ID NO: 48.

In some embodiments, the L-FR4 of the isolated antigen-binding protein comprises an amino acid sequence as set forth in SEQ ID NO: 14 or SEQ ID NO: 22.

In some embodiments, the isolated antigen-binding protein comprises an HCDR1, an HCDR2 and an HCDR3, the HCDR1 comprises the amino acid sequence as set forth in SEQ ID NO: 3, the HCDR2 comprises the amino acid sequence as set forth in SEQ ID NO: 2, and the HCDR3 comprises the amino acid sequence as set forth in SEQ ID NO: 1.

In some embodiments, the isolated antigen-binding protein comprises an LCDR1, an LCDR2 and an LCDR3, the LCDR1 comprises the amino acid sequence as set forth in SEQ ID NO: 6, the LCDR2 comprises the amino acid sequence as set forth in SEQ ID NO: 5, and the LCDR3 comprises the amino acid sequence as set forth in SEQ ID NO: 4. In some embodiments, the isolated antigen-binding protein comprises an HCDR1, an HCDR2, an HCDR3, an LCDR1, an LCDR2, and an LCDR3, the HCDR1 comprises the amino acid sequence as set forth in SEQ ID NO: 3, the HCDR2 comprises the amino acid sequence as set forth in SEQ ID NO: 2, the HCDR3 comprises the amino acid sequence as set forth in SEQ ID NO: 1, the LCDR1 comprises the amino acid sequence as set forth in SEQ ID NO: 6, the LCDR2 comprises the amino acid sequence as set forth in SEQ ID NO: 5, and the LCDR3 comprises the amino acid sequence as set forth in SEQ ID NO: 4.

In some embodiments, the isolated antigen-binding protein comprises a VH, and the VH comprises the amino acid sequence as set forth in SEQ ID NO: 49.

In some embodiments, the VH of the isolated antigen-binding protein comprises an amino acid sequence as set forth in any one of SEQ ID NO: 28, SEQ ID NO: 30, SEQ ID NO: 32, and SEQ ID NO: 34.

In some embodiments, the isolated antigen-binding protein comprises a VL, and the VL comprises an amino acid sequence as set forth in SEQ ID NO: 50.

In some embodiments, the VL of the isolated antigen-binding protein comprises an amino acid sequence as set forth in any one of SEQ ID NO: 29, SEQ ID NO: 31, and SEQ ID NO: 33.

In some embodiments, the isolated antigen-binding protein comprises any set of amino acid sequences selected from the group consisting of:

1) said VH comprises an amino acid sequence as set forth in SEQ ID NO: 28 and said VL comprises an amino acid sequence as set forth in SEQ ID NO: 29;
2) said VH comprises an amino acid sequence as set forth in SEQ ID NO: 30 and said VL comprises an amino acid sequence as set forth in SEQ ID NO: 31;
3) said VH comprises an amino acid sequence as set forth in SEQ ID NO: 30 and said VL comprises an amino acid sequence as set forth in SEQ ID NO: 33;
4) said VH comprises an amino acid sequence as set forth in SEQ ID NO: 32 and said VL comprises an amino acid sequence as set forth in SEQ ID NO: 31; and
5) said VH comprises an amino acid sequence as set forth in SEQ ID NO: 34 and said VL comprises an amino acid sequence as set forth in SEQ ID NO: 33.

In some embodiments, the isolated antigen-binding protein comprises an antibody heavy chain constant region.

In some embodiments, the antibody heavy chain constant region is derived from a human antibody heavy chain constant region.

In some embodiments, the antibody heavy chain constant region is derived from a human IgG heavy chain constant region.

In some embodiments, the antibody heavy chain constant region is derived from a human IgG1 heavy chain constant region.

In some embodiments, the antibody heavy chain constant region comprises an amino acid sequence as set forth in SEQ ID NO: 37.

In some embodiments, the isolated antigen-binding protein comprises an antibody light chain constant region.

In some embodiments, the antibody light chain constant region is derived from a human Igκ constant region.

In some embodiments, the antibody light chain constant region comprises an amino acid sequence as set forth in SEQ ID NO: 38.

In some embodiments, the isolated antigen-binding protein comprises an antibody or an antigen-binding fragment thereof.

In some embodiments, the antigen-binding fragment includes Fab, Fab', Fv fragment, $F(ab')_2$, $F(ab)_2$, scFv, di-scFv and/or dAb.

In some embodiments, the antibody is selected from one or more of the group consisting of a monoclonal antibody, a chimeric antibody, a humanized antibody, and a fully human antibody.

In some embodiments, the isolated antigen-binding protein is capable of specifically binding to the CD73 or a functionally active fragment thereof.

In some embodiments, the CD73 comprises a human CD73 and/or a monkey CD73.

In some embodiments, the isolated antigen-binding protein is capable of inhibiting the enzymatic activity of the CD73.

In some embodiments, the isolated antigen-binding protein is capable of inducing the endocytosis of the CD73 on the cell surface.

In some embodiments, the Tm and/or Tagg value of the isolated antigen-binding protein is higher than 65° C.

In some embodiments, the isolated antigen-binding protein has no or weak non-specific adsorption effect.

In some embodiments, the isolated antigen-binding protein is capable of inhibiting tumor growth.

In another aspect, this application further provides a polypeptide molecule comprising the isolated antigen-binding protein.

In some embodiments, the polypeptide molecule comprises a fusion protein.

In another aspect, this application further provides a nucleic acid molecule encoding the isolated antigen-binding protein or the polypeptide molecule.

In another aspect, this application further provides a vector comprising the nucleic acid molecule.

In another aspect, this application further provides an immunoconjugate comprising the isolated antigen-binding protein.

In another aspect, this application further provides a cell comprising the nucleic acid molecule, the vector and/or the immunoconjugate.

In another aspect, this application further provides a pharmaceutical composition comprising the isolated antigen-binding protein, the polypeptide molecule, the nucleic acid molecule, the vector, the immunoconjugate and/or the cell, and optionally a pharmaceutically acceptable carrier.

In another aspect, this application further provides a method for preparing the isolated antigen-binding protein, the method comprising culturing the cell under the condition that the isolated antigen-binding protein is expressed.

In another aspect, this application further provides a use of the isolated antigen-binding protein, the polypeptide molecule, the nucleic acid molecule, the vector, the immunoconjugate, the cell and/or the pharmaceutical composition in preparation of a medicament for preventing and/or treating a disease and/or disorder.

In some embodiments, the disease and/or disorder is mediated by the CD73.

In some embodiments, the disease and/or disorder include tumors.

In some embodiments, the tumors include solid tumors and/or hematomas.

In some embodiments, the disease and/or disorder includes breast cancer.

In another aspect, this application further provides a method for detecting the CD73 in a sample, comprising administering the isolated antigen-binding protein, the polypeptide molecule, the nucleic acid molecule, the vector, the immunoconjugate, the cell and/or the pharmaceutical composition.

In another aspect, this application further provides a reagent or kit for detecting the CD73 in a sample, comprising the isolated antigen-binding protein, the polypeptide molecule, the nucleic acid molecule, the vector, the immunoconjugate, the cell and/or the pharmaceutical composition.

In another aspect, this application further provides a use of the isolated antigen-binding protein, the polypeptide molecule, the nucleic acid molecule, the vector, the immunoconjugate, the cell and/or the pharmaceutical composition in preparation of a kit, and the kit is used for detecting the presence and/or content of CD73 in a sample.

Those skilled in the art can easily gain insight into other aspects and advantages of this application from the detailed description below. Only exemplary embodiments of this application are shown and described in the detailed description below. As will be appreciated by those skilled in the art, the content of this application enables those skilled in the art to make changes to the specific embodiments disclosed without departing from the spirit and scope of the invention referred to in this application. Accordingly, the descriptions in the drawings and specification of this application are only exemplary and not restrictive.

BRIEF DESCRIPTION OF THE DRAWINGS

The specific features of the invention referred to in this application are shown in the appended claim. The characteristics and advantages of the invention referred to in this application can be better understood by referring to the exemplary embodiments and drawings described in detail below. The accompanying drawings are briefly described as follows:

DETAILED DESCRIPTION OF THE PREFERRED EMBODIMENTS

Figure 1:
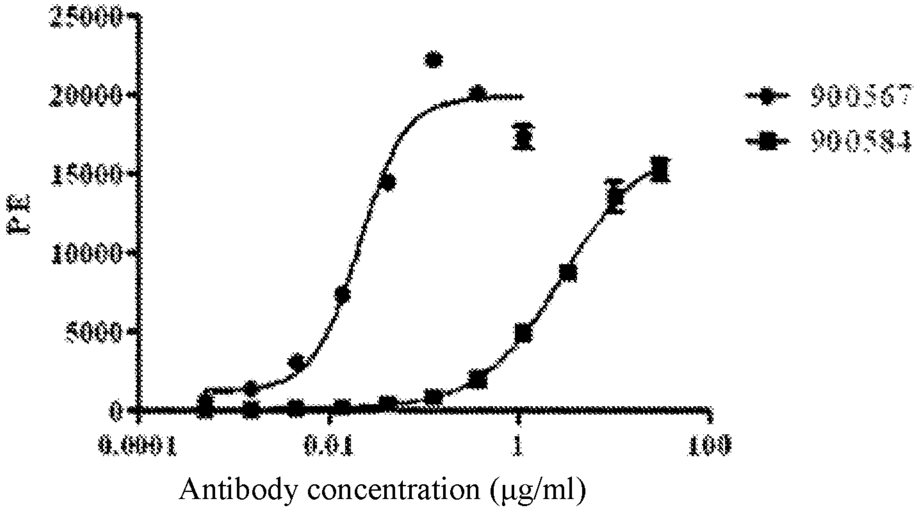
FIG. 1 shows the binding activity of an antigen-binding protein according to this application to a human CD73 on a cell surface.

Embodiments of the invention of this application will be described in the following specific examples, and those skilled in the art can easily understand other advantages and effects of the invention of this application from the content disclosed in this specification.

Terms and Definitions

In the present application, the term “CD73” used herein is also known as “NT5E”, “Cluster of Differentiation 73”, “5'-nucleotidase (5'-NT)” or “ecto-5'-nucleotidase”. The term covers “full length”, unprocessed CD73 as well as any form of CD73 produced by cellular processing. In this application, the term “CD73” includes full-length wild-type CD73 and mutants, fragments, variants, isoforms and homologues thereof. In some embodiments, the CD73 may include human CD73. For example, the sequence for human CD73 can be found under Uniprot accession number P21589.

In the present application, the term “isolated” used herein, refers to material that is artificially obtained from its natural environment. If an “isolated” substance or component occurs in nature, it may be that its natural environment has been altered, the substance has been isolated from its natural environment, or both. For example, a naturally-occurring polynucleotide or polypeptide present in a living animal is not isolated, but the same high-purity polynucleotide or polypeptide, separated from this natural environment, is isolated. The term “isolated” does not exclude the admixture of artificial or synthetic substances, nor the presence of other impure substances which do not affect the activity of the sub stance.

In the present application, the term "isolated antigen-binding protein" used herein generally refers to a protein having antigen-binding ability that is removed from its naturally occurring environment. The "isolated antigen-binding protein" may include an antigen-binding moiety and, optionally, a framework or framework portion that permits the antigen-binding moiety to adopt a conformation that facilitates binding of the antigen-binding moiety to antigen. Antigen-binding proteins may include, for example, antibody-derived protein framework regions (FR) or alternative protein framework regions or artificial framework regions with grafted CDRs or CDR derivatives. Such frameworks include, but are not limited to, antibody-derived framework regions comprising mutations introduced, e.g., to stabilize the three-dimensional structure of the antigen-binding protein, and fully synthetic framework regions comprising, e.g., biocompatible polymers. (see, e.g., Korndorfer, et al., 2003, Proteins: Structure, Function, and Bioinformatics, 53 (1):121-129 (2003); Roque, et al., Biotechnol. Prog. 20:639-654 (2004)). Examples of the antigen-binding protein include, but are not limited to: human antibodies, humanized antibodies; chimeric antibodies; recombinant antibodies; single-chain antibodies; diabodies; triabodies; tetrabodies; Fab, Fab', Fv fragments, $F(ab')_2$, $F(ab)_2$, scFv, di-scFv, dAb, and IgD antibodies; IgE antibodies; IgM antibodies; IgG1 antibodies; IgG2 antibodies; IgG3 antibodies; or IgG4 antibodies and fragments thereof.

In the present application, the term "CDR" or "complementarity determining region" generally refers to a region in the variable domain of an antibody, the sequence of which is highly variable and/or forms a structure-defining loop. In general, there are six CDRs in an antibody, three (HCDR1, HCDR2, and HCDR3) in each VH and three (LCDR1, LCDR2, and LCDR3) in each VL. In some embodiments, naturally occurring camelid antibodies consisting only of heavy chains are capable of functioning and stabilizing in the absence of light chains (see, e.g., Hamers-Casterman et al., Nature 363:446-448 (1993); Sheriff et al., Nature Struct. Biol. 3:733-736 (1996)). Antibody CDRs can be identified by a variety of coding systems, such as CCG, Kabat, Chothia, and IMGT, and Kabat/Chothia may be preferred after comprehensive consideration. These coding systems are known in the art, see, for example, http://www.bioinforg.uk/abs/index.html#kabatnum. For example, the amino acid sequences of the antigen-binding protein can be numbered according to the IMGT numbering scheme (IMGT, the international ImMunoGeneTics information system@imgt.cines.fr; http://imgt.cines.fr; Lefranc et al., 1999, Nucleic Acids Res. 27: 209-212; Ruiz et al., 2000 Nucleic Acids Res. 28: 219-221; Lefranc, et al., 2001, Nucleic Acids Res. 29:207-209; Lefranc, et al., 2003, Nucleic Acids Res. 31: 307-310; Lefranc, et al., 2005, DevComp Immunol 29: 185-203). For example, the CDRs of the antigen-binding protein can be numbered according to (see, e.g., Kabat E A & Wu T T (1971) Ann NY AcadSci 190:382-391 and Kabat E A, et al., (1991) Sequences of Proteins of Immunological Interest, Fifth Edition, U.S. Department of Health and Human Services, NIH Publication No. 91-3242).

In the present application, the term "framework region" or "FR" used herein generally refers to the more highly conserved portions of antibody variable domains, known as the framework regions. In general, there are four FRs (H-FR1, H-FR2, H-FR3 and H-FR4) in each naturally occurring heavy-chain variable region, and four FRs (L-FR1, L-FR2, L-FR3 and L-FR4) in each naturally occurring light-chain variable region.

In the present application, the terms "variable domain" and "variable region" are used interchangeably and generally refer to a portion of a heavy and/or light chain of an antibody. The variable domains of the heavy and light chains may be referred to as "$V_H$" and "$V_L$," respectively (or "VH" and "VL," respectively). These domains are usually the most variable parts of an antibody (relative to other antibodies of the same class), and comprise antigen-binding sites.

In the present application, the term "variable" used herein generally refers to that some segments of the variable domain may be quite different in sequence between antibodies. The variable domains mediate antigen binding and determine the specificity of a particular antibody to its particular antigen. However, the variability is not evenly distributed throughout the variable domains. It is usually concentrated in three segments, known as hypervariable regions (CDRs or HVRs), in the light-chain and heavy-chain variable domains. A more highly conserved portion in the variable domain is called a framework (FR). The variable domains of naturally occurring heavy and light chains each comprise four FR regions, most adopting a β-sheet configuration, connected by three CDRs, which form a circular connection and in some cases form part of the β-sheet structure. The CDRs in each chain are closely brought together by the FR, and form, together with the CDRs from another chain, an antigen-binding site of the antibody (see Kabat et al., Sequences of Immunological Interest, Fifth Edition, National Institute of Health, Bethesda, Md. (1991)).

In the present application, the term "antibody" used herein generally refers to an immunoglobulin or a fragment or derivative thereof and encompasses any polypeptide that includes antigen-binding sites, whether produced in vitro or in vivo. The term includes, but is not limited to, polyclonal, monoclonal, monospecific, multi specific, non-specific, humanized, single-stranded, chimeric, synthetic, recombinant, hybrid, mutated and transplanted antibodies. Unless otherwise modified by the term "intact", as in "intact antibody", the term "antibody" also includes antibody fragments for the purposes of the present invention, such as Fab, $F(ab')_2$, Fv, scFv, Fd, dAb and other antibody fragments that maintain antigen binding function (e.g., specific binding to human CD73). Typically, such fragments will include the antigen binding domains. A basic 4-chain antibody unit is a heterotetrameric glycoprotein composed of two identical light (L) chains and two identical heavy (H) chains. An IgM antibody consists of 5 basic heterotetrameric units and another polypeptide called J chain, and contain 10 antigen-binding sites, while an IgA antibody includes 2-5 4-chain antibody units that can bind to J chains to form a multivalent structure. For an IgG, the 4-chain unit is typically about 150,000 Daltons. Each L chain is linked to an H chain by a covalent disulfide bond, while two H chains are linked to each other by one or more disulfide bonds depending on the H chain isotype. Each H and L chain also has regularly spaced intrachain disulfide bridges. Each H chain has a variable domain (VH) at the N terminal, followed by three constant domains (CH) for the α and γ chains respectively and four CH domains for the μ and isoforms respectively. Each L chain has a variable domain (VL) at the N terminal and a constant domain at its other end. VL corresponds to VH, and CL corresponds to the first constant domain (CH1) of the heavy chain. Certain amino acid residues are believed to form an interface between the light-chain and heavy-chain variable domains. A VH and a VL pair together to form a single antigen-binding site. For the structure and properties of the different classes of antibodies, see, e.g., Basic and Clinical Immunology, 8th Edition, Daniel P. Sties, Abba I.

Terr and Tristram G Parsolw (eds), Appleton & Lange, Norwalk, Conn., 1994, page 71 and chapter 6. L chains from any vertebrate species can be classified into one of two distinct types, called κ and λ, based on the amino acid sequences of their constant domains. Depending on the amino acid sequences of the heavy chain (CH) constant domains, immunoglobulins can be assigned to different classes or isotypes. There are currently five classes of immunoglobulins: IgA, IgD, IgE, IgG and IgM, with heavy chains designated α, δ, ε, γ and μ, respectively.

In the present application, the term "antigen-binding fragment" used herein generally refers to one or more fragments that have the ability to specifically bind to an antigen (e.g., CD73). In this application, the antigen-binding fragment may include Fab, Fab', $F(ab)_2$, Fv fragments, $F(ab')_2$, scFv, di-scFv and/or dAb.

In the present application, the term "Fab" used herein generally refers to an antigen-binding fragment of an antibody. As described above, intact antibodies can be digested using papain as described above. The antibody is digested with papain to produce two identical antigen-binding fragments, i.e., a "Fab" fragment and a residual "Fc" fragment (i.e., the Fc region, ibid.). The Fab fragment may consist of an intact L chain, the variable region of a heavy chain and the first constant region (CH1) of the H chain (VH).

In the present application, the term "Fab' fragment" used herein generally refers to a monovalent antigen-binding fragment of a human monoclonal antibody, which is slightly larger than the Fab fragment. For example, the Fab' fragment may comprise all of the light chain, all of the variable domains of the heavy chain, and all or part of the first and second constant domains of the heavy chain. For example, the Fab' fragment used herein may also comprise part or all of the 220-330 amino acid residues of a heavy chain.

In the present application, the term "F(ab')2" generally refers to antibody fragments produced by pepsin digestion of intact antibodies. The F(ab')2 fragment comprises two Fab fragments and part of the hinge region held together by disulfide bonds. F(ab')2 fragments have bivalent antigen-binding activity and are capable of cross-linking antigen.

In the present application, the term "Fv fragment" used herein generally refers to a monovalent antigen-binding fragment of a human monoclonal antibody, comprising all or part of the heavy-chain and light-chain variable regions and lacking the heavy-chain and light-chain constant regions. The heavy-chain and light-chain variable regions include, for example, CDRs. For example, an Fv fragment comprises all or part of amino-terminal variable regions of about 110 amino acids of the heavy and light chains.

In the present application, the term "scFv" used herein generally refers to a fusion protein comprising at least one antibody fragment comprising a variable region of a light chain and at least one antibody fragment comprising a variable region of a heavy chain, where the light-chain and heavy-chain variable regions are contiguous (e.g. via a synthetic linker such as a short flexible polypeptide linker) and can be expressed as a single-chain polypeptide. Moreover, the scFv retains the specificity of the intact antibody from which it was derived. Unless otherwise specified, as used herein, the scFv can have the VL and VH regions in any order (e.g., relative to the N terminal and C terminal of the polypeptide), and the scFv may comprise VL-linker-VH or VH-Linker-VL.

In the present application, the term "dAb" used herein generally refers to an antigen-binding fragment having a VH domain and a VL domain, or having a VH domain or a VL domain (see e.g. Ward et al., (Nature, 1989 Oct. 12; 341 (6242): 544-6); see Holt et al., Trends Biotechnol., 2003, 21 (11): 484-490; and see, e.g., WO 06/030220, WO 06/003388 and other patent applications disclosed by Domantis Ltd.).

In the present application, the term "monoclonal antibody" used herein generally refers to a preparation of antibody molecules of single molecular composition. The monoclonal antibody is usually highly specific for a single antigenic site. Moreover, unlike conventional polyclonal antibody preparations, which often have different antibodies directed against different determinants, each monoclonal antibody is directed against a single determinant on the antigen. In addition to their specificity, the advantage of monoclonal antibodies lies in that they may be synthesized by hybridoma culture, without being contaminated by other immunoglobulins. The modifier "monoclonal" indicates the characteristics of an antibody obtained from a substantially homogeneous population of antibodies and is not construed as requiring that the antibody be produced by any particular method. For example, the monoclonal antibodies used herein may be prepared in hybridoma cells, or may be prepared by recombinant DNA methods.

In the present application, the term "chimeric antibody" used herein generally refers to an antibody in which the variable region is derived from one species and the constant region is derived from another species. Generally, the variable region is derived from an antibody ("parent antibody") in an experimental animal such as a rodent, and the constant region is derived from a human antibody, such that the resulting chimeric antibody is less likely to elicit an adverse immune response in an individual human than the parental (e.g., mouse-derived) antibody.

In the present application, the term "humanized antibody" used herein generally refers to an antibody in which some or all of the amino acids outside the CDR of a non-human antibody (e.g., a mouse antibody) have been replaced by corresponding amino acids derived from human immunoglobulins. In the CDR, small additions, deletions, insertions, substitutions or modifications of amino acids may also be allowed so long as they still retain the ability of the antibody to bind to a specific antigen. A humanized antibody may optionally comprise at least a portion of a constant region of a human immunoglobulin. The "humanized antibody" retains antigen specificity similar to that of the original antibody. The "Humanized" form of a non-human antibody (e.g., mouse antibody) may minimally comprise a chimeric antibody derived from a non-human immunoglobulin sequence. In some cases, CDR residues in a human immunoglobulin (receptor antibody) may be replaced with CDR residues from a nonhuman species (donor antibody) (such as a mouse, a rat, a rabbit, or a non-human primate) with the desired properties, affinity, and/or capability. In some cases, FR residues of the human immunoglobulin may be replaced with corresponding non-human residues. In addition, the humanized antibody may comprise amino acid modifications that are absent in the recipient antibody or in the donor antibody. These modifications may be made to further improve the properties, such as binding affinity, of the antibody.

The term "fully human antibody" used herein generally refers to an antibody that comprises only human immunoglobulin protein sequences. The fully human antibody may comprise murine sugar chains if it is produced in mice, in mouse cells, or in hybridomas derived from mouse cells. Similarly, a "mouse antibody" or "rat antibody" refers to an antibody comprising only mouse or rat immunoglobulin sequences, respectively. The fully human antibody can be produced in humans and in transgenic animals with human immunoglobulin germline sequences, by phage display technology or other molecular biology methods. Exemplary technologies that can be used to make antibodies have been described in U.S. Pat. Nos. 6,150,584, 6,458,592, and 6,420,140. Other techniques, such as using libraries, are known in the art.

In the present application, the terms "polypeptide," "peptide" and "protein" used herein are used interchangeably to refer to polymers of amino acid residues. The term "fusion protein" used herein generally refers to a polypeptide having at least two portions covalently linked together, where each of the portions is a polypeptide having a different property. The property may be a biological property, such as activity in vitro or in vivo. The property can also be simple chemical or physical property, such as binding to a target molecule, catalysis of a reaction, etc. The two portions can be linked directly by a single peptide bond or through a peptide linker.

In the present application, the term "nucleic acid molecule" used herein generally refers to nucleotides, deoxyribonucleotides or ribonucleotides of any length in isolated form, or analogs isolated from their natural environment or artificially synthesized.

In the present application, the term "vector" used herein generally refers to a nucleic acid delivery vehicle into which a polynucleotide encoding a protein can be inserted and the protein can be expressed. The vector can be expressed by transforming, transducing or transfecting the host cell, so that the genetic material elements carried thereon can be expressed in the host cell. For example, vectors can include: plasmids; phagemids; cosmids; artificial chromosomes such as yeast artificial chromosome (YAC), bacterial artificial chromosome (BAC) or P1-derived artificial chromosome (PAC); phage such as λ phage or M13 phages and animal viruses, etc. Animal virus species used as vectors may include retroviruses (including lentiviruses), adenoviruses, adeno-associated viruses, herpesviruses (such as herpes simplex virus), poxviruses, baculoviruses, papillomaviruses, and papovavirus (such as SV40). A vector may comprise a variety of elements that control expression, including promoter sequence, transcriptional initiation sequence, enhancer sequence, selective element and reporter gene. In addition, the vector may also comprise replication initiation sites. Vectors may also include components that assist their entry into cells, such as, but not exclusively, viral particles, liposomes, or protein coats.

In the present application, the term "cell" generally refers to an individual cell, a cell line or a cell culture that can be or has been the receptor of a subject's plasmid or vector, and it comprises the nucleic acid molecule of the present invention or the vector of the present invention. The cell may include a progeny of an individual cell. Due to natural, accidental or deliberate mutations, the progeny cell may not be necessarily identical (either in the morphology of the total DNA complement or in the genome) to the original parent cell. The cell may be obtained by transfecting a cell in vitro using the vector of this application. The cell may be bacterial cells (e.g. *E. coli*), yeast cells or other eukaryotic cells such as COS cells, Chinese Hamster Ovary (CHO) cells, CHO-K1 cells, LNCAP cells, HeLa cells, HEK293 cells, COS-1 cells, and NS0 cells. In some embodiments, the cells are mammalian cells. In some embodiments, the mammalian cells are HEK293 cells.

In the present application, the term "immunoconjugate" used herein generally refers to a conjugate formed by conjugating (e.g., covalently linking with a linker molecule) the other agent (e.g., chemotherapeutics, radioactive elements, cytostatic and cytotoxic agents) to the antibody or the antigen-binding fragment thereof. The conjugate can deliver the other agent to the target cell (e.g., a tumor cell) through specific binding of the antibody or an antigen-binding fragment thereof to an antigen on the target cell.

In the present application, the term "pharmaceutical composition" used herein generally refers to a composition for preventing/treating a disease or disorder. The pharmaceutical composition may comprise the isolated antigen-binding protein of this application, the nucleic acid molecule of this application, the vector of this application and/or the cell of this application, and optionally a pharmaceutically acceptable adjuvant. In addition, the pharmaceutical composition may also comprise suitable preparations of one or more (pharmaceutically effective) carriers, stabilizers, excipients, diluents, solubilizers, surfactants, emulsifiers and/or preservatives. The acceptable components of the compositions are preferably nontoxic to recipients at the dosages and concentrations employed. The pharmaceutical compositions of the present invention include, but are not limited to, liquid, frozen and lyophilized compositions.

In the present application, the term "pharmaceutically acceptable carrier" used herein generally includes pharmaceutically acceptable carriers, excipients or stabilizers that are nontoxic for cells or mammals to which they are exposed at the dosages and concentrations employed. The physiologically acceptable carriers may include, for example, buffers; antioxidants; low-molecular-weight (less than about 10 residues) polypeptides; proteins; hydrophilic polymers; amino acids; monosaccharides; disaccharides and other carbohydrates; chelating agents; sugar alcohols; salt-forming counterions such as sodium; and/or nonionic surfactants.

In the present application, the term "specific binding" or "specific to . . . " used herein generally refers to a measurable and reproducible interaction, such as the binding between a target and an antibody, whereby the existence of a target may be determined in the presence of a heterogeneous population of molecules (including biomolecules) For example, an antibody specifically binding to a target (which may be an epitope) may be an antibody that binds to that target with greater affinity, avidity, easier, and/or for a longer duration than it binds to other targets. In some embodiments, the antibody specifically binds to an epitope on a protein that is conservative among proteins of different species. In some embodiments, the specific binding includes, but does not require exclusive binding.

In the present application, the term "subject" used herein generally refers to human or non-human animals, including but not limited to cats, dogs, horses, pigs, cows, sheep, rabbits, mice, rats or monkeys.

The term "tumor" used herein generally refers to any new pathological growth of tissue. Tumor cells can spread to other parts of the body locally or through the bloodstream and lymphatic system. In this application, the tumor may include benign tumors and malignant tumors. In this application, the tumor may include solid tumors and/or hematological tumors. In this application, the tumor may include cancers. In this application, examples of the tumor may include, but not limited to: breast cancer.

In the present application, the term "no or weak non-specific electrostatic binding" used herein generally means that the isolated antigen-binding protein has almost no non-specific adsorption effect on non-target molecules. For example, the SPR method can be used to measure the non-specific adsorption effect between the isolated antigen-binding protein and the non-target molecules. After the effect of Buffer is deducted, the signal intensity of the isolated antigen-binding protein of this application is less than or close to 20 RU. Generally, it can be considered that the interaction between the antigen-binding protein and the non-target molecules is weak when the signal intensity is below about 20 RU, for example, about 20 RU, about 19 RU, about 18 RU, about 17 RU, about 16 RU, about 15 RU, about 14 RU, about 13 RU, about 12 RU, about 11 RU, about 10 RU, about 9 RU, about 8 RU, about 7 RU, about 6 RU, about 5 RU, about 4 RU, about 3 RU, about 2 RU or about 1 RU, the interaction between the antigen-binding protein and the non-target molecules is strong when the signal intensity is greater than about 20 RU, and the interaction between the antigen-binding protein and the non-target molecules is very strong when the signal intensity is greater than about 100 RU.

In the present application, the proteins, polypeptides and/or amino acid sequences involved should also be understood to include at least the following scope: variants or homologues having the same or similar functions as the proteins or polypeptides.

In the present application, the variant may be a protein or polypeptide formed by substituting, deleting or adding one or more amino acids in an amino acid sequence of the defined protein and/or polypeptide (for example, an antibody or a fragment thereof that specifically binds to the CD73 protein). For example, the functional variant may comprise a protein or polypeptide with amino acid changes induced by substituting, deleting, and/or inserting at least one amino acid, for example, 1-30, 1-20, or 1-1033 amino acids, and for another example, 1, 2, 3, 4, or 5 amino acids. The functional variant may substantially maintain the biological properties of the protein or polypeptide before the changes (e.g., substitution, deletion, or addition). For example, the functional variants may maintain at least 60%, 70%, 80%, 90%, or 100% of the biological activity (e.g., the ability of binding to an antigen) of the defined protein or the polypeptide before the changes. For example, the substitution may be conservative substitution.

In the present application, the homologue may be a protein or polypeptide that has at least about 85% (for example, at least about 85%, about 90%, about 91%, about 92%, about 93%, about 94%, about 95%, about 96%, about 97%, about 98%, about 99% or higher) sequence homology with the amino acid sequence of the defined protein and/or polypeptide (e.g., an antibody or a fragment thereof that specifically binds to the CD73 protein).

In the present application, the homology generally refers to the similarity, resemblance or association between two or more sequences. The "percentage of sequence homology" may be calculated in the following way: comparing the two sequences to be aligned in a comparison window; determining, in the two sequences, the number of positions at which identical nucleic acid bases (for example, A, T, C, G) or identical amino acid residues (for example, Ala, Pro, Ser, Thr, Gly, Val, Leu, Ile, Phe, Tyr, Trp, Lys, Arg, His, Asp, Glu, Asn, Gln, Cys, and Met) exist to acquire the number of matching positions; and dividing the number of matching positions by the total number of positions in the comparison window (i.e., the window size); and multiplying a result by 100 to produce the percentage of sequence homology. The alignment for determining the percentage of sequence homology may be achieved in a variety of ways known in the art, for example, by using publicly available computer software such as BLAST, BLAST-2, ALIGN or Megalign (DNASTAR) software. Those skilled in the art may determine appropriate parameters for sequence alignment, including any algorithm required to implement the maximum alignment undergoing comparison, within a full-length sequence range or within a target sequence region. The homology may also be determined by the following methods: FASTA and BLAST. For the description of the FASTA algorithm, a reference may be made to W. R. Pearson and D. J. Lipman, "Improved Tools for Biological Sequence Comparison", Proc. Natl. Acad. Sci.), 85: 2444-2448, 1988: and D. J. Lipman and W. R. Pearson, "Rapid and Sensitive Protein Similarity Searches", Science, 227: 1435-1441, 1989. For the description of the BLAST algorithm, a reference may be made to S. Altschul, W. Gish, W. Miller, E. W. Myers and D. Lipman, "Basic Local Alignment Search Tool", Journal of Molecular Biology, 215: 403-410, 1990.

In the present application, the term "comprise" generally refers to the meaning of including, inclusive, containing, or encompassing. In some cases, it also means "is/are" and "consist of".

In the present application, the term "about" generally refers to a variation within a range of 0.5%-10% above or below a specified value, for example, a variation within a range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% above or below a specified value.

DETAILED DESCRIPTION OF THE INVENTION

Isolated Antigen-Binding Protein

The CDR of an antibody, also known as the complementarity determining region, is a portion of the variable region. The amino acid residues in this region may make contacts with the antigen or antigenic epitope. Antibody CDRs can be determined by a variety of coding systems, such as CCG, Kabat, Chothia, and IMGT, and Kabat/Chothia may be preferred after comprehensive consideration. These coding systems are known in the art, see, for example, http://www.bioinf.org.uk/abs/index.html#kabatnum. Those skilled in the art can use different coding systems to determine the CDRs according to the sequence and structure of the antibody. There may be differences in the CDRs using different coding systems. In this application, the CDRs used therein may include CDR sequences obtained according to any CDR division method. The CDRs may also include their variants, and the variants include substitutions, deletions and/or additions of one or more amino acids to the amino acid sequences of the CDRs. The variants may include substitutions, deletions and/or additions of, for example, 1-30, 1-20 or 1-10 amino acids, and for example, 1, 2, 3, 4, 5, 6, 7, 8 or 9 amino acids, to the amino acid sequences of the CDRs. The CDRs may also include homologues having percent sequence identity of at least about 85% (e.g., at least about 85%, about 90%, about 91%, about 92%, about 93%, about 94%, about 95%, about 96%, about 97%, about 98%, about 99% or higher) to the amino acid sequences of the CDRs. In some embodiments, the CDRs are identified by the IMGT numbering scheme.

In one aspect, this application provides an isolated antigen-binding protein comprising at least one CDR in a heavy-chain variable region VH, the VH comprising an amino acid sequence as set forth in SEQ ID NO: 49. The isolated antigen-binding protein used herein may comprise CDRs obtained by dividing the amino acid sequence as set forth in SEQ ID NO: 49 in any manner.

In this application, the isolated antigen-binding protein may comprise an HCDR3, and the HCDR3 may comprise an amino acid sequence as set forth in SEQ ID NO: 1.

In this application, the isolated antigen-binding protein may comprise an HCDR2, and the HCDR2 may comprise an amino acid sequence as set forth in SEQ ID NO: 2.

In this application, the isolated antigen-binding protein may comprise an HCDR1, and the HCDR1 may comprise an amino acid sequence as set forth in SEQ ID NO: 3.

In this application, the isolated antigen-binding protein may comprise an HCDR1, an HCDR2 and an HCDR3. For example, the HCDR1 of the isolated antigen-binding protein may comprise the amino acid sequence as set forth in SEQ ID NO: 3, the HCDR2 may comprise the amino acid sequence as set forth in SEQ ID NO: 2, and the HCDR3 may comprise the amino acid sequence as set forth in SEQ ID NO: 1.

In this application, the isolated antigen-binding protein may comprise at least one CDR in a light-chain variable region VL, and the VL comprises an amino acid sequence as set forth in SEQ ID NO: 50.

In this application, the isolated antigen-binding protein may comprise an LCDR3, and the LCDR3 may comprise, for example, an amino acid sequence as set forth in SEQ ID NO: 4.

In this application, the isolated antigen-binding protein can also comprise an LCDR2, and the LCDR2 may comprise, for example, an amino acid sequence as set forth in SEQ ID NO: 5.

In this application, the isolated antigen-binding protein can also comprise an LCDR1, and the LCDR1 may comprise, for example, an amino acid sequence as set forth in SEQ ID NO: 6.

In this application, the isolated antigen-binding protein can also comprise an LCDR1, an LCDR2 and an LCDR3. For example, the LCDR1 of the isolated antigen-binding protein may comprise the amino acid sequence as set forth in SEQ ID NO: 6, the LCDR2 may comprise the amino acid sequence as set forth in SEQ ID NO: 5, and the LCDR3 may comprise the amino acid sequence as set forth in SEQ ID NO: 4.

In this application, the isolated antigen-binding protein may comprise an HCDR1, an HCDR2, an HCDR3, an LCDR1, an LCDR2 and an LCDR3. For example, the HCDR1 of the isolated antigen-binding protein used herein may comprise the amino acid sequence as set forth in SEQ ID NO: 3, the HCDR2 may comprise the amino acid sequence as set forth in SEQ ID NO: 2, the HCDR3 may comprise an amino acid sequence as set forth in SEQ ID NO: 1, the LCDR1 comprises an amino acid sequence as set forth in SEQ ID NO: 6, the LCDR2 may comprise the amino acid sequence as set forth in SEQ ID NO: 5, and the LCDR3 may comprise the amino acid sequence as set forth in SEQ ID NO: 4.

In this application, the isolated antigen-binding protein may comprise an H-FR1, a C terminal of the H-FR1 can be directly or indirectly linked to an N terminal of the HCDR1, and the H-FR1 may comprise, for example, an amino acid sequence as set forth in SEQ ID NO: 41. For example, the H-FR1 may comprise an amino acid sequence as set forth in any one of SEQ ID NO: 7, SEQ ID NO: 15 and SEQ ID NO: 23.

In this application, the isolated antigen-binding protein may comprise an H-FR2, and the H-FR2 can be located between the HCDR1 and the HCDR2 and comprise, for example, an amino acid sequence as set forth in SEQ ID NO: 42. For example, the H-FR2 may comprise an amino acid sequence as set forth in SEQ ID NO: 8 or SEQ ID NO: 16.

In this application, the isolated antigen-binding protein may comprise an H-FR3, and the H-FR3 can be located between the HCDR2 and the HCDR3 and comprise, for example, an amino acid sequence as set forth in SEQ ID NO: 43. For example, the H-FR3 may comprise an amino acid sequence as set forth in any one of SEQ ID NO: 9, SEQ ID NO: 17, SEQ ID NO: 24 and SEQ ID NO: 27.

In some embodiments, the isolated antigen-binding protein may comprise an H-FR4, an N terminal of the H-FR4 can be linked to a C terminal of the HCDR3, and the H-FR4 may comprise, for example, an amino acid sequence as set forth in SEQ ID NO: 44. For example, the H-FR4 may comprise an amino acid sequence as set forth in SEQ ID NO: 10 or SEQ ID NO: 18.

In this application, the isolated antigen-binding protein may comprise an H-FR1, an H-FR2, an H-FR3 and an H-FR4. For example, the H-FR1, the H-FR2, the H-FR3 and the H-FR4 of the isolated antigen-binding protein can sequentially comprise the amino acid sequences as set forth in SEQ ID NO: 41, SEQ ID NO: 42, SEQ ID NO: 43 and SEQ ID NO: 44, respectively.

For example, the H-FR1, the H-FR2, the H-FR3 and the H-FR4 of the isolated antigen-binding protein can sequentially comprise the amino acid sequences as set forth in SEQ ID NO: 7, SEQ ID NO: 8, SEQ ID NO: 9 and SEQ ID NO: 10, respectively. For example, the H-FR1, the H-FR2, the H-FR3 and the H-FR4 of the isolated antigen-binding protein can sequentially comprise the amino acid sequences as set forth in SEQ ID NO: 15, SEQ ID NO: 16, SEQ ID NO: 17 and SEQ ID NO: 18, respectively. For example, the H-FR1, the H-FR2, the H-FR3 and the H-FR4 of the isolated antigen-binding protein can sequentially comprise the amino acid sequences as set forth in SEQ ID NO: 23, SEQ ID NO: 16, SEQ ID NO: 24 and SEQ ID NO: 18, respectively. For example, the H-FR1, the H-FR2, the H-FR3 and the H-FR4 of the isolated antigen-binding protein can sequentially comprise the amino acid sequences of SEQ ID NO: 23, SEQ ID NO: 16, SEQ ID NO: 27 and SEQ ID NO: 18, respectively.

In this application, the isolated antigen-binding protein may comprise an L-FR1, a C terminal of the L-FR1 can be directly or indirectly linked to an N terminal of the LCDR1, and the L-FR1 may comprise, for example, an amino acid sequence as set forth in SEQ ID NO: 45. For example, the L-FR1 may comprise an amino acid sequence as set forth in any one of SEQ ID NO: 11, SEQ ID NO: 19 and SEQ ID NO: 25.

In this application, the isolated antigen-binding protein may comprise an L-FR2, and the L-FR2 can be located between the LCDR1 and the LCDR2 and comprise, for example, an amino acid sequence as set forth in SEQ ID NO: 46. For example, the L-FR2 may comprise an amino acid sequence as set forth in SEQ ID NO: 12 or SEQ ID NO: 20.

In this application, the isolated antigen-binding protein may comprise an L-FR3, and the L-FR3 can be located between the LCDR2 and the LCDR3 and comprise, for example, an amino acid sequence as set forth in SEQ ID NO: 47. For example, the L-FR3 may comprise an amino acid sequence as set forth in any one of SEQ ID NO: 13, SEQ ID NO: 21 and SEQ ID NO: 26.

In this application, the isolated antigen-binding protein may comprise an L-FR4, and an N terminal of the L-FR4 can be linked to a C terminal of the LCDR3 and the L-FR4 may comprise, for example, an amino acid sequence as set forth in SEQ ID NO: 48. For example, the L-FR4 may comprise an amino acid sequence as set forth in SEQ ID NO: 14 or SEQ ID NO: 22.

In this application, the isolated antigen-binding protein may comprise an L-FR1, an L-FR2, an L-FR3, and an L-FR4. For example, the L-FR1, the L-FR2, the L-FR3 and the L-FR4 of the isolated antigen-binding protein can sequentially comprise the amino acid sequences as set forth in SEQ ID NO: 45, SEQ ID NO: 46, SEQ ID NO: 47 and SEQ ID NO: 48, respectively.

For example, the L-FR1, the L-FR2, the L-FR3 and the L-FR4 of the isolated antigen-binding protein can sequentially comprise the amino acid sequences as set forth in SEQ ID NO: 11, SEQ ID NO: 12, SEQ ID NO: 13 and SEQ ID NO: 14, respectively. For example, the L-FR1, the L-FR2, the L-FR3 and the L-FR4 of the isolated antigen-binding protein can sequentially comprise the amino acid sequences as set forth in SEQ ID NO: 19, SEQ ID NO: 20, SEQ ID NO: 21 and SEQ ID NO: 22, respectively. For example, the L-FR1, the L-FR2, the L-FR3 and the L-FR4 of the isolated antigen-binding protein can sequentially comprise the amino acid sequences as set forth in SEQ ID NO: 25, SEQ ID NO: 20, SEQ ID NO: 26 and SEQ ID NO: 22, respectively.

In this application, the isolated antigen-binding protein may comprise an VH, and the VH may comprise an amino acid sequence as set forth in SEQ ID NO: 49. For example, the VH may comprise an amino acid sequence as set forth in any one of SEQ ID NO: 28, SEQ ID NO: 30, SEQ ID NO: 32, and SEQ ID NO: 34.

In this application, the isolated antigen-binding protein may comprise a VL, and the VL may comprise an amino acid sequence as set forth in SEQ ID NO: 50. For example, the VL may comprise an amino acid sequence as set forth in SEQ ID NO: 29, SEQ ID NO: 31 or SEQ ID NO: 33.

In this application, the isolated antigen-binding protein may comprise a VH and a VL. For example, the VH may comprise the amino acid sequence as set forth in SEQ ID NO: 49 and the VL may comprise the amino acid sequence as set forth in SEQ ID NO: 50.

For example, the VH may comprise the amino acid sequence as set forth in SEQ ID NO: 28 and the VL may comprise the amino acid sequence as set forth in SEQ ID NO: 29. For example, the VH may comprise the amino acid sequence as set forth in SEQ ID NO: 30 and the VL may comprise the amino acid sequence as set forth in SEQ ID NO: 31. For example, the VH may comprise the amino acid sequence as set forth in SEQ ID NO: 30 and the VL may comprise the amino acid sequence as set forth in SEQ ID NO: 33. For example, the VH may comprise the amino acid sequence as set forth in SEQ ID NO: 32 and the VL may comprise the amino acid sequence as set forth in SEQ ID NO: 31. For example, the VH may comprise the amino acid sequence as set forth in SEQ ID NO: 34 and the VL may comprise the amino acid sequence as set forth in SEQ ID NO: 33.

In this application, the isolated antigen-binding protein may comprise an antibody heavy chain constant region. In this application, the antibody heavy chain constant region can be derived from a human IgG heavy chain constant region. In some embodiments, the isolated antigen-binding protein comprises an antibody heavy chain constant region and the antibody heavy chain constant region is derived from a human IgG1 heavy chain constant region. In this application, the antibody heavy chain constant region also includes its variants, homologues, and analogs. For example, the CH2 of the human IgG1 heavy chain constant region carries L234A and L235A (Eu numbering) mutations of the antibody ADCC knockout (KO) effect. For example, the antibody heavy chain constant region may comprise an amino acid sequence as set forth in SEQ ID NO:37.

For example, the HCDR1, the HCDR2 and the HCDR3 of the isolated antigen-binding protein can sequentially comprise the amino acid sequences as set forth in SEQ ID NO: 3, SEQ ID NO: 2 and SEQ ID NO: 1, respectively, and the heavy chain constant region of the isolated antigen-binding protein may comprise the amino acid sequence as set forth in SEQ ID NO: 37.

For example, the HCDR1, the HCDR2 and the HCDR3 of the isolated antigen-binding protein can sequentially comprise the amino acid sequences as set forth in SEQ ID NO: 3, SEQ ID NO: 2 and SEQ ID NO: 1, respectively, the H-FR1, the H-FR2, the H-FR3 and the H-FR4 of the isolated antigen-binding protein can sequentially comprise the amino acid sequences as set forth in SEQ ID NO: 41, SEQ ID NO: 42, SEQ ID NO: 43 and SEQ ID NO: 44, respectively, and the heavy chain constant region of the isolated antigen-binding protein may comprise the amino acid sequence as set forth in SEQ ID NO: 37.

For example, the HCDR1, the HCDR2 and the HCDR3 of the isolated antigen-binding protein can sequentially comprise the amino acid sequences as set forth in SEQ ID NO: 3, SEQ ID NO: 2 and SEQ ID NO: 1, respectively, the H-FR1, the H-FR2, the H-FR3 and the H-FR4 of the isolated antigen-binding protein can sequentially comprise the amino acid sequences as set forth in SEQ ID NO: 7, SEQ ID NO: 8, SEQ ID NO: 9 and SEQ ID NO: 10, respectively, and the heavy chain constant region of the isolated antigen-binding protein may comprise the amino acid sequence as set forth in SEQ ID NO: 37.

For example, the HCDR1, the HCDR 2 and the HCDR 3 of the isolated antigen-binding protein can sequentially comprise the amino acid sequences as set forth in SEQ ID NO: 3, SEQ ID NO: 2 and SEQ ID NO: 1, respectively, and the H-FR1, the H-FR2, the H-FR3 and the H-FR4 of the isolated antigen-binding protein can sequentially comprise the amino acid sequences as set forth in SEQ ID NO: 15, SEQ ID NO: 16, SEQ ID NO: 17 and SEQ ID NO: 18, respectively, and the heavy chain constant region of the isolated antigen-binding protein may comprise the amino acid sequence as set forth in SEQ ID NO: 37.

For example, the HCDR1, the HCDR2 and the HCDR3 of the isolated antigen-binding protein can sequentially comprise the amino acid sequences as set forth in SEQ ID NO: 3, SEQ ID NO: 2 and SEQ ID NO: 1, respectively, and the H-FR1, the H-FR2, the H-FR3 and the H-FR4 of the isolated antigen-binding protein can sequentially comprise the amino acid sequences as set forth in SEQ ID NO: 23, SEQ ID NO: 16, SEQ ID NO: 24 and SEQ ID NO: 18, respectively, and the heavy chain constant region of the isolated antigen-binding protein may comprise the amino acid sequence as set forth in SEQ ID NO: 37.

For example, the HCDR1, the HCDR2 and the HCDR3 of the isolated antigen-binding protein can sequentially comprise the amino acid sequences as set forth in SEQ ID NO: 3, SEQ ID NO: 2 and SEQ ID NO: 1, respectively, the H-FR1, the H-FR2, the H-FR3 and the H-FR4 of the isolated antigen-binding protein can sequentially comprise the amino acid sequences as set forth in SEQ ID NO: 23, SEQ ID NO: 16, SEQ ID NO: 27 and SEQ ID NO: 18, respectively, and the heavy chain constant region may comprise an amino acid sequence as set forth in SEQ ID NO:37.

For example, the VH of the isolated antigen-binding protein may comprise the amino acid sequence as set forth in SEQ ID NO: 49, and the heavy chain constant region of the isolated antigen-binding protein may comprise the amino acid sequence as set forth in SEQ ID NO: 37.

For example, the VH of the isolated antigen-binding protein may comprise the amino acid sequence as set forth in SEQ ID NO: 28, and the heavy chain constant region of the isolated antigen-binding protein may comprise the amino acid sequence as set forth in SEQ ID NO: 37.

For example, the VH of the isolated antigen-binding protein may comprise the amino acid sequence as set forth in SEQ ID NO: 30, and the heavy chain constant region of the isolated antigen-binding protein may comprise the amino acid sequence as set forth in SEQ ID NO: 37.

For example, the VH of the isolated antigen-binding protein may comprise the amino acid sequence as set forth in SEQ ID NO: 32, and the heavy chain constant region of the isolated antigen-binding protein may comprise the amino acid sequence as set forth in SEQ ID NO: 37.

For example, the VH of the isolated antigen-binding protein may comprise the amino acid sequence as set forth in SEQ ID NO: 34, and the heavy chain constant region of the isolated antigen-binding protein may comprise the amino acid sequence as set forth in SEQ ID NO: 37.

In this application, the isolated antigen-binding protein may comprise an antibody light chain constant region. In this application, the antibody light chain constant region can be derived from a human Igκ constant region. For example, the antibody light chain constant region may comprise an amino acid sequence set forth in SEQ ID NO: 38.

For example, the LCDR1, the LCDR2 and the LCDR3 of the isolated antigen-binding protein can sequentially comprise the amino acid sequences as set forth in SEQ ID NO: 6, SEQ ID NO: 5 and SEQ ID NO: 4, respectively, and the light chain constant region of the isolated antigen-binding protein may comprise the amino acid sequence as set forth in SEQ ID NO: 38.

For example, the LCDR1, the LCDR2 and the LCDR3 of the isolated antigen-binding protein can sequentially comprise the amino acid sequences as set forth in SEQ ID NO: 6, SEQ ID NO: 5 and SEQ ID NO: 4, respectively, the L-FR1, the L-FR2, the H-FR3 and the L-FR4 of the isolated antigen-binding protein can sequentially comprise the amino acid sequences as set forth in SEQ ID NO: 45, SEQ ID NO: 46, SEQ ID NO: 47 and SEQ ID NO: 48, respectively, and the light chain constant region of the isolated antigen-binding protein may comprise the amino acid sequence as set forth in SEQ ID NO: 38.

For example, the LCDR1, the LCDR2 and the LCDR3 of the isolated antigen-binding protein can sequentially comprise the amino acid sequences as set forth in SEQ ID NO: 6, SEQ ID NO: 5 and SEQ ID NO: 4, respectively, the L-FR1, the L-FR2, the H-FR3 and the L-FR4 of the isolated antigen-binding protein can sequentially comprise the amino acid sequences as set forth in SEQ ID NO: 11, SEQ ID NO: 12, SEQ ID NO: 13, and SEQ ID NO: 14, respectively, and the light chain constant region of the isolated antigen-binding protein may comprise the amino acid sequence as set forth in SEQ ID NO: 38.

For example, the LCDR1, the LCDR2 and the LCDR3 of the isolated antigen-binding protein can sequentially comprise the amino acid sequences as set forth in SEQ ID NO: 6, SEQ ID NO: 5 and SEQ ID NO: 4, respectively, the L-FR1, the L-FR2, the H-FR3 and the L-FR4 of the isolated antigen-binding protein can sequentially comprise the amino acid sequences as set forth in SEQ ID NO: 19, SEQ ID NO: 20, SEQ ID NO: 21, and SEQ ID NO: 22, respectively, and the light chain constant region of the isolated antigen-binding protein may comprise the amino acid sequence as set forth in SEQ ID NO: 38.

For example, the LCDR1, the LCDR2 and the LCDR3 of the isolated antigen-binding protein can sequentially comprise the amino acid sequences set forth in SEQ ID NO: 6, SEQ ID NO: 5 and SEQ ID NO: 4, respectively, the L-FR1, the L-FR2, the H-FR3 and the L-FR4 of the isolated antigen-binding protein can sequentially comprise the amino acid sequences as set forth in SEQ ID NO: 25, SEQ ID NO: 20, SEQ ID NO: 26, and SEQ ID NO: 22, respectively, and the light chain constant region of the isolated antigen-binding protein may comprise the amino acid sequence as set forth in SEQ ID NO: 38.

For example, the VL of the isolated antigen-binding protein may comprise the amino acid sequence as set forth in SEQ ID NO: 50, and the light chain constant region of the isolated antigen-binding protein may comprise the amino acid sequence as set forth in SEQ ID NO: 38.

For example, the VL of the isolated antigen-binding protein may comprise the amino acid sequence as set forth in SEQ ID NO: 29, and the light chain constant region of the isolated antigen-binding protein may comprise the amino acid sequence as set forth in SEQ ID NO: 38.

For example, the VL of the isolated antigen-binding protein may comprise the amino acid sequence as set forth in SEQ ID NO: 50, and the light chain constant region of the isolated antigen-binding protein may comprise the amino acid sequence as set forth in SEQ ID NO: 38.

For example, the VL of the isolated antigen-binding protein may comprise the amino acid sequence as set forth in SEQ ID NO: 31, and the light chain constant region of the isolated antigen-binding protein may comprise the amino acid sequence as set forth in SEQ ID NO: 38.

For example, the VL of the isolated antigen-binding protein may comprise the amino acid sequence as set forth in SEQ ID NO: 33, and the light chain constant region of the isolated antigen-binding protein may comprise the amino acid sequence as set forth in SEQ ID NO: 38.

In this application, the isolated antigen-binding protein may comprise a VH, a VL, a heavy-chain constant region and a light-chain constant region. For example, the VH may comprise the amino acid sequence as set forth in SEQ ID NO: 49, the VL may comprise the amino acid sequence as set forth in SEQ ID NO: 50, the heavy chain constant region may comprise the amino acid sequence as set forth in SEQ ID NO: 37, and the light chain constant region may comprise the amino acid sequence as set forth in SEQ ID NO: 38. For example, the VH may comprise the amino acid sequence as set forth in SEQ ID NO: 28, the VL may comprise the amino acid sequence as set forth in SEQ ID NO: 29, the heavy chain constant region may comprise the amino acid sequence as set forth in SEQ ID NO: 37, and the light chain constant region may comprise the amino acid sequence as set forth in SEQ ID NO: 38. For example, the VH may comprise the amino acid sequence as set forth in SEQ ID NO: 30, the VL may comprise the amino acid sequence as set forth in SEQ ID NO: 31, the heavy chain constant region may comprise the amino acid sequence as set forth in SEQ ID NO: 37, and the light chain constant region may comprise the amino acid sequence as set forth in SEQ ID NO: 38. For example, the VH may comprise the amino acid sequence as set forth in SEQ ID NO: 30, the VL may comprise the amino acid sequence as set forth in SEQ ID NO: 33, the heavy chain constant region may comprise the amino acid sequence as set forth in SEQ ID NO: 37, and the light chain constant region may comprise the amino acid sequence as set forth in SEQ ID NO: 38. For example, the VH may comprise the amino acid sequence as set forth in SEQ ID NO: 32, the VL may comprise the amino acid sequence as set forth in SEQ ID NO: 31, the heavy chain constant region may comprise the amino acid sequence as set forth in SEQ ID NO: 37, and the light chain constant region may comprise the amino acid sequence as set forth in SEQ ID NO: 38. For example, the VH may comprise the amino acid sequence as set forth in SEQ ID NO: 34, the VL may comprise the amino acid sequence as set forth in SEQ ID NO: 33, the heavy chain constant region may comprise the amino acid sequence as set forth in SEQ ID NO: 37, and the light chain constant region may comprise the amino acid sequence as set forth in SEQ ID NO: 38.

In this application, the isolated antigen-binding protein may comprise an antibody or an antigen-binding fragment thereof.

In some embodiments, the antigen-binding fragment includes Fab, Fab', FIT fragment, $F(ab')_2$, $F(ab)_2$, scFv, di-scFv and/or dAb.

In some embodiments, the antibody includes a monoclonal antibody, a chimeric antibody, a humanized antibody, and fully human antibody.

For example, the VH of the chimeric antibody may comprise the amino acid sequence as set forth in SEQ ID NO: 28, and the VL of the chimeric antibody may comprise the amino acid sequence as set forth in SEQ ID NO: 29.

For example, the VH of the chimeric antibody may comprise the amino acid sequence as set forth in SEQ ID NO: 30, and the VL of the chimeric antibody may comprise the amino acid sequence as set forth in SEQ ID NO: 31.

For example, the VH of the chimeric antibody may comprise the amino acid sequence as set forth in SEQ ID NO: 30, and the VL of the chimeric antibody may comprise the amino acid sequence as set forth in SEQ ID NO: 33.

For example, the VH of the chimeric antibody may comprise the amino acid sequence as set forth in SEQ ID NO: 32, and the VL of the chimeric antibody may comprise the amino acid sequence as set forth in SEQ ID NO: 31.

For example, the VH of the chimeric antibody may comprise the amino acid sequence as set forth in SEQ ID NO: 34, and the VL of the chimeric antibody may comprise the amino acid sequence as set forth in SEQ ID NO: 33.

In addition, it should be noted that the isolated antigen-binding protein of this application may comprise heavy chain and/or light chain sequences with one or more conservative sequence modifications. The so-called "conservative sequence modification" refers to the amino acid modification that will not significantly affect or change the binding properties of the antibody. Such conservative modifications include amino acid substitutions, additions and deletions. Modifications can be introduced into the isolated antigen-binding protein of this application by standard techniques known in the art, such as point mutations and PCR-mediated mutagenesis. Conservative amino acid substitutions are substitutions of amino acid residues with amino acid residues with similar side chains. Groups of amino acid residues having similar side chains are known in the art. These groups of amino acid residues include amino acids with basic side chains (e.g., lysine, arginine, and histidine), acidic side chains (e.g., aspartic acid and glutamic acid), uncharged polar side chains (e.g., glycine, asparagine, glutamine, serine, threonine, tyrosine, cysteine, and tryptophan), nonpolar side chains (e.g., alanine, valine, leucine acid, isoleucine, proline, phenylalanine, and methionine), β-branched side chains (e.g. threonine, valine, and isoleucine) and aromatic side chains (e.g., tyrosine, phenylalanine, tryptophan, and histidine). In some embodiments, one or more amino acid residues in the CDR regions of the isolated antigen-binding protein of this application may be replaced with other amino acid residues from the same side chain group. Those skilled in the art know that some conservative sequence modifications do not abolish antigen binding, see, e.g., Brummelletal., et al., (1993) Biochem 32:1180-8; de Wildt et al., (1997) Prot. Eng. 10:835-41; Komissarov et al., (1997) J. Biol. Chem. 272:26864-26870; Hall et al., (1992) J. Immunol. 149:1605-12; Kelley and O'Connell (1993) Biochem.32:6862-35; Adib-Conquy et al., (1998) Int. Immunol. 10:341-6 and Beers et al., (2000) Clin. Can. Res. 6:2835-43.

The CD73 antigen-binding protein of this application can be identified, screened, or characterized by various assays known in the art.

For example, the antigen-binding protein of this application or the antigen binding activity of the fusion protein can be tested by known methods such as enzyme-linked immunosorbent assay (ELISA), immunoblotting (e.g., Western blot), flow cytometry (e.g., FACS), immunohistochemistry, immunofluorescence, etc.

In this application, the isolated antigen-binding protein is capable of specifically bind to CD73 or a functionally active fragment thereof.

In some embodiments, the isolated antigen-binding protein was subjected to affinity screening by Biacore. The isolated antigen-binding protein can bind to the CD73 protein with a KD of $3\times10^{-9}$M or lower. For example, the antigen-binding protein described in the application can bind with a KD of less than about $3\times10^{-9}$M, less than about $2\times10^{-9}$M, less than about $1\times10^{-9}$M, less than about $7\times10^{-10}$M, less than about $6\times10^{-10}$M, less than about $5\times10^{-10}$M, less than about $4\times10^{-10}$M, less than about $3\times10^{-10}$M, less than about $2\times10^{-10}$M, less than about $1\times10^{-10}$M, less than about $9\times10^{-11}$M, less than about $5\times10^{-11}$M, or less than about $2\times10^{-11}$M. In some embodiments, this application also includes the use of FACS to determine the binding activity of the antigen-binding protein to an antigen. For example, the antigen-binding protein described therein can bind to a human CD73 on the cell surface with an EC50 value less than or equal to 0.3 μg/mL, less than or equal to about 0.2 μg/mL, less than or equal to about 0.1 μg/mL, less than or equal to about 0.09 μg/mL, less than or equal to about 0.08 μg/mL, less than or equal to about 0.07 μg/mL, less than or equal to about 0.06 μg/mL, less than or equal to about 0.05 μg/mL, less than or equal to about 0.04 μg/mL, less than or equal to about 0.03 μg/mL, less than or equal to about 0.02 μg/mL or less than or equal to about 0.01 μg/mL.

For example, the antigen-binding protein described therein can bind to a recombinant CD73 protein with an EC50 value less than or equal to 0.4 μg/mL, less than or equal to 0.3 μg/mL, less than or equal to about 0.2 μg/mL, less than or equal to about 0.1 μg/mL, less than or equal to about 0.09 μg/mL, less than or equal to about 0.08 μg/mL, less than or equal to about 0.07 μg/mL, less than or equal to about 0.06 μg/mL, less than or equal to about 0.05 μg/mL, less than or equal to about 0.04 μg/mL, less than or equal to about 0.03 μg/mL, less than or equal to about 0.02 μg/mL or less than or equal to about 0.01 μg/mL.

In some embodiments, the isolated antigen-binding protein is capable of inhibiting the CD73. In some embodiments, the antigen-binding protein of this application can also cross-react with a monkey CD73, and the titer can be detected by, e.g., FACS. The term "cross-react" used herein generally refers to the ability of an antibody to react with homologous proteins from other species.

In some embodiments, the isolated antigen-binding protein of this application does not bind to a mouse and/or rat CD73.

The titer can be detected by, e.g., ELISA. For example, the binding activity or functional activity of the isolated antigen-binding protein can be detected using FACS. For example, an affinity test can be performed on the isolated antigen-binding protein.

In this application, the isolated antigen-binding protein is capable of inhibiting the enzymatic activity of CD73. For example, the isolated antigen-binding protein may have an inhibitory effect on the enzymatic activity of the recombinant CD73. For example, the isolated antigen-binding protein may have an inhibitory effect on the enzymatic activity of the human CD73. The enzyme activity described herein can be tested by any method commonly used in the art. The testing of the enzyme activity may include mixing the CD73 antigen-binding protein with the recombinant CD73 protein, adding AMP and ATP, adding a CellTiter-Glo® substrate to a CellTiter-Glo® buffer, mixing and equilibrating the resulting solution to react at room temperature, and carrying out a full-wavelength test. For example, the antigen-binding protein described therein can inhibit the enzymatic activity of the recombinant CD73 protein with an EC50 value less than or equal to about 0.1 μg/mL, less than or equal to about 0.09 μg/mL, less than or equal to about 0.08 μg/mL, less than or equal to about 0.07 μg/mL, less than or equal to about 0.06 μg/mL, less than or equal to about 0.05 μg/mL, less than or equal to about 0.04 μg/mL, less than or equal to about 0.03 μg/mL, less than or equal to about 0.02 μg/mL, or less than or equal to about 0.01 μg/mL. For example, the antigen-binding protein described therein can the enzymatic activity of the CD73 protein on the cell membrane with an EC50 value less than or equal to 0.2 μg/mL, less than or equal to about 0.1 μg/mL, less than or equal to about 0.09 μg/mL, less than or equal to about 0.08 μg/mL, less than or equal to about 0.07 μg/mL, less than or equal to about 0.06 μg/mL, less than or equal to about 0.05 μg/mL, less than or equal to about 0.04 μg/mL, less than or equal to about 0.03 μg/mL, less than or equal to about 0.02 μg/mL, or less than or equal to about 0.01 μg/mL.

In this application, the isolated antigen-binding protein is capable of inducing the endocytosis of the CD73 on the cell surface. In some embodiments, the endocytosis of the protein can be determined by fluorescent labeling. For example, flow cytometry can be used to detect the fluorescence intensity of cells to obtain the efficiency of the antigen-binding protein inducing the endocytosis of CD73 on the cell surface. In certain instances, the isolated antigen-binding protein can induce endocytosis of CD73 with an efficiency of about 50% or higher.

In this application, the isolated antigen-binding protein can be thermally stable. For example, a protein stability analyzer can be used to detect the melting temperature (Tm) and/or aggregation temperature (Tagg) of the antigen-binding protein of this application. The Tm value of the isolated antigen-binding protein of this application is greater than or equal to about 65° C., greater than or equal to about 66° C., greater than or equal to about 67° C., greater than or equal to about 68° C., greater than or equal to about 69° C., greater than or equal to about 69.4° C., greater than or equal to about 70° C., or greater than or equal to about 70.2° C. The Tagg value of the isolated antigen-binding protein of this application is greater than or equal to about 65° C., greater than or equal to about 66° C., greater than or equal to about 66.4° C., greater than or equal to about 67° C., greater than or equal to about 68° C., greater than or equal to about 69° C., greater than or equal to about 70° C., greater than or equal to about 71° C., greater than or equal to about 72° C., greater than or equal to about 73° C., greater than or equal to about 74° C., greater than or equal to about 74.1° C., greater than or equal to about 75° C. or greater than or equal to about 75.6° C.

In this application, the isolated antigen-binding protein can have no or weak non-specific adsorption effect. For example, the SPR method can be used to measure the non-specific adsorption effect between the isolated antigen-binding protein and the non-target molecules. After the effect of Buffer is deducted, the signal intensity of the isolated antigen-binding protein of this application is less than or close to 20 RU. Generally, it can be considered that the signal intensity is below about 20 RU, for example, about 20 RU, about 19 RU, about 18 RU, about 17 RU, about 16 RU, about 15 RU, about 14 RU, about 13 RU, about 12 RU, about 11 RU, about 10 RU, about 9 RU, about 8 RU, about 7 RU, about 6 RU, about 5 RU, about 4 RU, about 3 RU, about 2 RU or about 1 RU.

In this application, the isolated antigen-binding protein can have the effect of inhibiting tumor growth.

Polypeptide Molecule, Nucleic Acid Molecule, Vector, Immunoconjugate, Cell, and Pharmaceutical Composition In another aspect, this application provides a polypeptide molecule which may comprise the isolated antigen-binding protein of this application.

In some embodiments, the polypeptide molecule comprises a fusion protein.

In another aspect, this application provides an isolated nucleic acid molecule capable of encoding the isolated antigen-binding protein of this application or the polypeptide molecule of this application. For example, the isolated nucleic acid molecule may be produced or synthesized by the following methods: (i) in vitro amplification, for example by polymerase chain reaction (PCR) amplification, (ii) clonal recombination, (iii) purification, for example, by fractionation through restriction digestion and gel electrophoresis, or (iv) synthesis, for example, by chemical synthesis.

In another aspect, this application provides a vector, which may comprise the nucleic acid molecule of this application. In addition, the vector may further comprise other genes, for example, a marker gene that is allowed to select this vector in a suitable host cell and under a suitable condition. In addition, the vector may also comprise an expression control element that allows a coding region to be expressed correctly in a suitable host. Such a control element is well known to those skilled in the art, which, for example, may include a promoter, a ribosome binding site, an enhancer, and other control elements that regulate gene transcription or mRNA translation. The vector can be expressed by transforming, transducing or transfecting the host cell, so that the genetic material elements carried thereon can be expressed in the host cell. The vector may comprise, for example, a plasmid, a cosmid, a virus, a bacteriophage, or other vectors commonly used in, for example, genetic engineering. For example, the vector is an expression vector. In addition, the vector can also include components that assist its entry into cells, such as, but not exclusively, viral particles, liposomes, or protein coats.

In another aspect, this application further provides an immunoconjugate which may comprise the isolated antigen-binding protein of this application.

For example, the isolated antigen-binding protein of this application or a fragment thereof can be linked to another agent, such as a chemotherapeutic agent, a toxin, an immunotherapeutic agent, an imaging probe, a spectroscopic probe, and the like. The "linked" can be achieved by one or more covalent bonds, or non-covalent interactions, and can include chelation. A variety of linkers, which may be known in the art, can be used to form immunoconjugates. Additionally, the immunoconjugates can be provided in the form of fusion proteins, which can be expressed from polynucleotides encoding the immunoconjugates. The immunoconjugates can also comprise, for example, antibody-drug conjugates (ADCs). Suitable drugs may include cytotoxins, alkylating agents, DNA minor groove binding molecules, DNA intercalators, DNA crosslinkers, histone sirtuin inhibitors, nuclear export inhibitors, proteasome inhibitors, inhibitors of topoisomerase I or II, heat shock protein inhibitors, tyrosine kinase inhibitors, antibiotics and antimitotic agents. In the ADCs, antibodies and therapeutic agents can be cross-linked by linkers that are cleavable, such as peptide, disulfide, or hydrazone linkers.

In another aspect, this application provides a cell, which may comprise the nucleic acid molecule of this application, the vector of this application and/or the immunoconjugate of this application. In some embodiments, each type of or each host cell comprises one or one type of the nucleic acid molecule or vector of this application. In some embodiments, each type of or each host cell may comprise a plurality of (for example, 2 or more) or a plurality of types of (for example, 2 or more types of) vectors of this application. For example, the vector of this application may be introduced into the host cell, for example, an eukaryotic cell, such as a plant-originated cell, a fungal cell, or a yeast cell, etc. In some embodiments, the cell is a bacterial cell (e.g., *E. coli*), a yeast cell, or other eukaryotic cells, such as a COS cell, a CHO cell, a CHO-K1 cell, an LNCAP cell, a HeLa cell, a 293T cell, a COS-1 cell, an SP2/0 cell, an NSO cell or a myeloma cell. The vector of this application may be introduced into the host cell by methods known in the art, such as electroporation, lipofectine transfection, lipofectamin transfection, etc.

In another aspect, this application further provides a pharmaceutical composition which may comprise the isolated antigen-binding protein of this application, the polypeptide molecule of this application, the immunoconjugate of this application, the nucleic acid molecule of this application, the vector of this application and/or the cell of this application, and optionally a pharmaceutically acceptable carrier.

In this application, the pharmaceutical composition can further comprise suitable preparations of one or more (pharmaceutically effective) adjuvants, stabilizers, excipients, diluents, solubilizers, surfactants, emulsifiers and/or preservatives. The acceptable components of the compositions are preferably nontoxic to recipients at the dosages and concentrations employed. The pharmaceutical composition of this application includes, but is not limited to, liquid, frozen and lyophilized compositions.

In this application, the pharmaceutical composition can further comprise more than one active compound, which generally refers to those active compounds with complementary activities that do not adversely affect each other. The type and effective amount of such drug may depend, for example, on the amount and type of antagonists present in the drug preparation, as well as the clinical parameters of the subject.

In this application, the pharmaceutically acceptable carrier can include any and all solvents, dispersion media, coatings, isotonic agents and absorption delaying agents compatible with drug administration, and are generally safe and non-toxic.

In this application, the pharmaceutical composition may be administered by routes including parenteral, transdermal, intracavity, intraarterial, intrathecal and/or intranasal administration or may be directly injected into tissues. For example, the pharmaceutical composition can be administered to a patient or subject by infusion or injection. In some embodiments, the pharmaceutical composition may be administered by different means, such as intravenous, intraperitoneal, subcutaneous, intramuscular, topical or intradermal administration. In some embodiments, the pharmaceutical composition can be administered without interruption. The uninterrupted (or continuous) administration can be achieved by a small pump system worn by the patient to measure the influx of a therapeutic agent into a patient, as described in WO2015/036583.

Preparation Method

In another aspect, this application provides a preparation method for the antigen-binding protein. The method may comprise culturing the host cell of this application under such a condition that the antigen-binding protein is expressed. For example, an appropriate medium, an appropriate temperature, a culture time and the like may be used, and these methods are understood by those of ordinary skills in the art.

Any method suitable for producing a monoclonal antibody may be used to produce the antigen-binding protein of this application. For example, animals may be immunized with linked or naturally occurring CD73 or fragments thereof. Suitable immunization methods may be used, including adjuvants, immunostimulants, and repeated booster immunizations, and one or more routes may be used. For example, a hybridoma preparation method can be used to obtain splenocytes from immunized mice for fusion with SP2/0 myeloma cells, and select hybridoma cell lines through HAT screening.

Any suitable form of CD73 can be used as an immunogen (antigen) to produce a non-human antibody specific to CD73 and to screen the biological activity of the antibody. For example, the eliciting immunogen may be a full-length mature human CD73, comprising natural homodimers, or peptides containing single/multiple epitopes. The immunogen may be used alone, or in combination with one or more immunogenicity enhancers known in the art.

A chimeric human antibody may be selected from any class of immunoglobulins, including IgM, IgD, IgG IgA, and IgE. In this application, the antibody may be an IgG antibody, and an IgG1 subtype may be used. An essential constant domain sequence may be optimized by screening antibodies with the biological assays described in the Examples below, so as to produce the desired biological activity. Similarly, any type of light chain may be used in the compounds and methods herein. For example, a K chain or its variants may be used in the compounds and methods of this application.

Method and Use

In another aspect, this application further provides a use of the isolated antigen-binding protein, the polypeptide molecule, the nucleic acid molecule, the vector, the immunoconjugate, the cell and/or the pharmaceutical composition in preparation of a medicament for preventing and/or treating a disease and/or disorder.

In another aspect, this application further provides a method for preventing and/or treating a disease and/or disorder. The method may comprise administering the isolated antigen-binding protein, the polypeptide molecule, the nucleic acid molecule, the vector, the immunoconjugate, the cell and/or the pharmaceutical composition of this application to a subject in need.

In this application, the administration may be carried out by different means, such as intravenous, intratumoral, intraperitoneal, subcutaneous, intramuscular, topical or intradermal administration.

In another aspect, the isolated antigen-binding protein, the polypeptide molecule, the nucleic acid molecule, the vector, the immunoconjugate, the cell and/or the pharmaceutical composition, as described therein, can be used for preventing and/or treating a disease and/or disorder.

In this application, the disease and/or disorder may be a CD73-mediated disease and/or disorder.

In this application, the disease and/or disorder may include tumors.

In this application, the tumors may include solid tumors and/or hematological tumors.

In this application, the disease and/or disorder may include breast cancer.

In another aspect, this application further provides a method for detecting the CD73 in a sample. The method comprises administering the isolated antigen-binding protein, the polypeptide molecule, the nucleic acid molecule, the vector, the cell, the immunoconjugate and/or the pharmaceutical composition.

In this application, the method for detecting CD73 in a sample may be an in vitro method. In the present application, the method for detecting CD73 in a sample may be for non-therapeutic purposes. In this application, the method for detecting CD73 in a sample is not a diagnostic method.

In another aspect, this application further provides a reagent or kit for detecting the CD73 in a sample, comprising the isolated antigen-binding protein, the polypeptide molecule, the nucleic acid molecule, the vector, the immunoconjugate, the cell and/or the pharmaceutical composition.

In another aspect, this application further provides a use of the isolated antigen-binding protein, the polypeptide molecule, the nucleic acid molecule, the vector, the immunoconjugate, the cell and/or the pharmaceutical composition in preparation a kit, and the kit is used for detecting the presence and/or content of CD73 in a sample.

Without wishing to be bound by any particular theory, it is believed that the following examples are merely to illustrate the antigen-binding protein, preparation method, uses and the like of this application, and are not intended to limit the scope of this application.

EXAMPLES

Example 1 Preparation Method of Anti-Human CD73 Murine Antigen-Binding Proteins 1.1 Preparation of Hybridoma Cells for Producing Murine Antigen-Binding Protein The method for preparing the murine monoclonal antigen-binding proteins was based on the hybridoma preparation technology invented by Kohler and Milstein in 1975 (Nature, 1975, 256: 495-497). First, human CD73 with His tag proteins (Met 1-Lys 547) was used as the immunization antigen. Part of the immunization antigen was used for immunization with Freund's Adjuvant, Complete (Sigma cat no. F5881, also known as FCA) and Freund's Adjuvant, Incomplete (Sigma cat no. F5506, also known as FICA) and the other part was used for subcutaneous immunization with Quick Antibody—Mouse 5w (Biodragoncat no.KX0210041) adjuvant to multiple BALB/c and CD1 mice respectively at multiple sites. After three immunizations, the serum was collected to detect the titer by ELISA, and to detect the binding activity and functional activity by FACS. Finally, spleen cells were removed from the selected optimal mice to fuse with SP2/0 myeloma cells. After HAT screening to select hybridoma cell strains, monoclonal hybridoma cell strains capable of specifically binding to human CD73 and monkey CD73 were screened out from the obtained cell culture supernatant by using the FACS method; then, monoclonal cell strains capable of inhibiting the enzyme activity of CD73 were screened out again and the screened monoclonal cell strains were subjected to affinity (Biacore) screening to finally obtain monoclonal hybridoma cell strains expressing the human CD73 antigen-binding protein; and the monoclonal hybridoma cell strains were subjected to sequence analysis. The functional activity and affinity results are shown in Table 1.

TABLE 1

Hybridoma screening data

| | Antigen-antibody binding activity | | | |
|---|---|---|---|---|
| Clone No. | Human CD73 MFI value | Monkey CD73 MFI value | Function activity | Affinity (KD) |
| 124A9 | 5031 | 3116 | 9.91 | 2.16E−09 |

After high-throughput screening, the finally obtained monoclonal hybridoma cell strains had high affinity and exhibited the binding activity to both humans and monkeys and the blocking function against the enzyme activity of CD73.

Example 2 Variable Region Gene Sequencing of Anti-CD73 Antigen-Binding Protein and Preparation of Antigen-Binding Proteins 2.1 Variable Region Gene Sequencing and Cloning of Antigen-Binding Proteins in Hybridoma Cells Based on the principle of TAKARA's 5' RACE technology, the cDNA sequences of the variable regions of the mouse antigen-binding protein expressed by the hybridoma cell strain 124A9 were cloned. Briefly, the variable region gene-specific cDNAs of the heavy and light chains were synthesized by using the SMARTer 5'RACE synthesis kit (TAKARA, #634859) according to the instructions. The 5'- and 3'-terminals of the cDNA sequences were modified with PCR primers which were designed to add appropriate leader sequences to the variable region cDNAs of the heavy and light chains, respectively, such that the resulting PCR products could be cloned, by a seamless cloning method, onto a heavy-chain vector pHB-Fc and a light-chain vector pHB-Cκ which are expressed in the existing recombinant antigen-binding protein. The expression vector pHB-Fc contained the human IgG1 heavy-chain constant region gene sequence, with L234A and L235A (Eu numbering) mutations of the antigen-binding protein ADCC knock out (KO) effect on CH2, and the vector pHB-Cκ contained the human κ light-chain constant region gene sequence. The PCR amplification products of the heavy- and light-chain variable regions were cloned into the expression vectors by means of an In-fusion cloning reagent (TAKARA, #639650), and transformed into *E. coli* DH5α competent cells (Yeastern Biotech, #FYE607-80VL). Monoclonal colonies were picked for Sanger and NGS sequencing, and the variable region sequences of the antigen-binding protein were obtained by analysis. The variable region sequences of the anti-CD73 antigen-binding protein expressed by 124A9 were as follows;

124A9 VH
SEQ ID NO: 28
QVQLQQPGAELVKPGASVKLSCKASGYTFTSYWIHWVKQRPGQGLDWIGM

IHPNSGSTYYNEKFKSKATLTVDKSSSTAYMQLSSLTSEDSAVYYCARYY

GSDYEWYFDVWGTGTTVTVSS

124A9 VL
SEQ ID NO: 29
DIVMTQSQKFMSTSVGDRVSITCKASQNVRTAVVWYQQNPGQSPKALIY

LASNRHTGVPDRFTGSGSGTDFTLTISNVHSEDLADYFCLQHWNYPYTFG

GGTKLEIK

The underlined sections were CDRs (as defined by IMGT, the sequences of CDRs were as follows):

TABLE 2

CDR sequences of mouse CD73 antigen-binding protein

| Domain | | Sequence | SEQ ID NO. |
|---|---|---|---|
| VH | CDR1 | GYTFTSYW | SEQ ID NO. 3 |
| | CDR2 | IHPNSGST | SEQ ID NO. 2 |
| | CDR3 | ARYYGSDYEWYFDV | SEQ ID NO. 1 |
| VL | CDR1' | QNVRTA | SEQ ID NO. 6 |
| | CDR2' | LAS | SEQ ID NO. 5 |
| | CDR3' | LQHWNYPYT | SEQ ID NO. 4 |

2.2 Expression of antigen-Binding Protein

The expression vectors obtained in 2.1 were amplified by means of *Escherichia coli*, and a sufficient amount of plasmids were prepared using an endotoxin-free plasmid extraction kit (Tiangen Biotech (Beijing) Co., Ltd., #DP117) for transient transfection to express the antigen-binding protein. CHO-S cells (ThermoFisher, #R80007) were used as host cells for expression. The two prepared heavy-chain vectors, respectively together with the light-chain vectors, were mixed with polyetherimide (PEI, Polysciences, #24765-1) to form liposome complexes, which were transfected into CHO-S cells and incubated in an incubator for 5-7 days. The cell culture supernatant was collected by centrifugation, and purified by a Protein A affinity chromatographic column to obtain a human-mouse antigen-binding protein (the antigen-binding protein expressed by 124A9 was numbered as 900567).

2.3 Preparation of Antigen-Binding Proteins 900725-900728

The antigen-binding protein was humanized by using a 3D modeling method as follows. First, the three-dimensional structure modeling of the mouse antigen-binding protein was carried out to select the optimal structural model. Specifically, Discovery Studio and Schrödinger Antibody Modeling were used. 5-10 optimal structural solutions were selected by using the homology modeling method. The Loop region was generally modeled using the homology modeling method. If the CDR amino acid sequence alignment results showed that the Identity was less than 50%, the CDR3 structure model was built using the ab initio modeling method. Ten antibody crystal structure models with the closest sequence (the structural resolution is higher than 2.5 angstroms) were retrieved by using PDBBLAST. The optimal structure model was selected by comparing with the automatic modeling models. The variable region sequence of the antigen-binding protein was aligned with available sequences in the NCBI IgBlast database, and by means of identification and analysis, a human framework region (FR) suitable for constructing CDR-grafted heavy and light chains thereon was finally determined.

During transformation, transformation sites were designed according to the conserved amino acid residues in the FR of the human antibody and the important amino acid residues in the FR of the antibody. The variable regions of the heavy and light chains of the antigen-binding protein 900567 of this application were respectively designed for humanized mutations, and the designed humanized sequences should meet the requirements of not affecting the structural stability of the antibody, not affecting the binding of the antigen-binding protein to the antigen, not introducing protein modification sites for glycosylation, phosphorylation and the like, and not introducing sites that are easily oxidized and aminated, enhancing structural stability, and the like. After analysis, a total of three humanized heavy chain sequences and three humanized light chain sequences were designed for the mouse antigen-binding protein sequence of 900567. The humanized point-mutation antigen-binding protein expression plasmids were expressed in the CHO-S cells and then purified respectively to obtain humanized antigen-binding proteins. The humanized antigen-binding proteins were screened in terms of receptor binding capability, functional inhibitory activity, non-specific binding properties, thermal stability and other indicators by using ELISA, Biacore, flow cytometry and other detection methods, and four humanized anti-CD73 antigen-binding proteins with excellent properties were obtained. The VH and VL sequences of the resulting anti-CD73 antigen-binding proteins were shown as follows:

900725 and 900726 VH
SEQ ID NO: 30
QVQLVQSGAEVKKPGASVKLSCKASGYTFTSYWIHWVRQAPGQGLEWIGM

IHPNSGSTYYNEKFKGRATLTVDKSTSTAYMELSSLRSEDTAVYYCARYY

GSDYEWYFDVWGQGTTVTVSS 900725 and 900727 VL
SEQ ID NO: 31
DIQMTQSPSSMSASVGDRVTITCKASQNVRTAVVWYQQKPGKAPKALIY

LASNRHTGVPDRFSGSGSGTDFTLTISSLQPEDFATYFCLQHWNYPYTFG

QGTKLEIK

900727 VH
SEQ ID NO: 32
QVQLVQSGAEVKKPGASVKVSCKASGYTFTSYWIHWVRQAPGQGLEWIG

MIHPNSGSTYYAQKFQGRVTITVDKSTSTAYMELSSLRSEDTAVYYC

ARYYGSDYEWYFDVWGQGTTVTVSS 900726 and 900728 VL
SEQ ID NO: 33
DIQMTQSPSSLSASVGDRVTITCKASQNVRTAVVWYQQKPGKAPKALIY

LASNRHTGVPDRFSGSGSGTDFTLTISSLQPEDFATYYCLQHWNYPYTF

GQGTKLEIK

900728 VH
SEQ ID NO: 34
QVQLVQSGAEVKKPGASVKVSCKASGYTFTSYWIHWVRQAPGQGLEWIG

MIHPNSGSTYYNEKFQGRVTMTVDKSTSTAYMELSSLRSEDTAVYYC

ARYYGSDYEWYFDVWGQGTTVTVSS

The underlined sections were CDRs (defined according to IMGT), and 900725, 900726, 900727 and 900728 were the numbers for the four humanized antibody proteins respectively.

Example 3 Testing on Binding Activity of Anti-CD73 Antigen-Binding Proteins to Cells Expressing Human CD73

The binding activity of anti-CD73 antigen-binding proteins 900567, 900584, 900725, 900726, 900727 and 900728 to cells (CHOK1-huCD73-3F4, Huabo Biopharm) expressing the human CD73 was tested. 900584 was the screened antigen-binding protein targeting CD73. The VH amino acid sequence of 900584 was as set forth in SEQ ID NO: 35 and the VL amino acid sequence of 900584 was as set forth in SEQ ID NO: 36.

All antigen-binding proteins were diluted to 30 μg/ml with 1% BSA in PBS solution (1% BSA/PBS) and then 3-fold diluted for 11 gradients. The diluted antigen-binding proteins were added to a 96-well U-shaped plate at 20 μL per well; and a negative control (with 1% BSA/PBS added only) was set up at the same time. The suspension of cells (CHOK1-huCD73-3F4, Huabo Biopharm) expressing human CD73 during the logarithmic growth phase were centrifuged (1000 rpm×5 min) to discard the culture medium; and the cells were resuspended with 1% BSA/PBS until the density of viable cells was $1\times10^6$/mL, and were added, at 20 μL ($2\times10^4$ cells) per well, to the 96-well U-shaped plate with the anti-CD37 antigen-binding protein to react for 30 min at room temperature. After reaction, the 96-well U-shaped plate was resuspended with 1% BSA/PBS, centrifuged (300 g×3 min) to discard the supernatant, and washed once in such a way. PE-goat anti-human-Fc (Jackson ImmunoResearch, #109-115098) diluted at 1:200 was added to react for 15 min in the dark at room temperature. After reaction, the 96-well U-shaped plate was resuspended with 1% BSA/PBS, centrifuged (300 g×3 min) to discard the supernatant, washed three times in such a way, and finally resuspended with 100 μL of 1% BSA/PBS for each wall; and the fluorescence intensity of a PE channel was detected with a flow cytometer (BD, #Cantoll).

The results of the binding activity of 900567 were shown in FIG. 1 and Table 3, and the results of the binding activity of 900567, 900725, 900726 and 900728 were shown in Table 4. The results showed that 900567 had good affinity to cells expressing human CD73, and 900725 and 900728 were comparable with 900567 in terms of affinity to cells (CHOK1-huCD73-3F4, Huabo Biopharm) expressing human CD73.

TABLE 3

Binding activity of 900567 and 900584 to human CD73 on the cell surface

| Antibody | 900567 | 900584 |
|---|---|---|
| EC50 (ug/mL) | 0.02096 | 2.904 |

TABLE 4

Binding activity of 900567 and 900725-900728 to human CD73 on the cell surface

| Antibody | 900567 | 900725 | 900726 | 900728 |
|---|---|---|---|---|
| EC50 (ug/mL) | 0.06497 | 0.1063 | 0.1736 | 0.1054 |

Example 4 Testing on Binding Activity of Anti-CD73 Antigen-Binding Proteins to Recombinant CD73 Protein The binding activity of anti-CD73 antigen-binding proteins 900567, 900725, 900726, 900727 and 900728 to a recombinant CD73 protein (ACRO, #CD3-H52H7-100 μg) was tested.

The ELISA well plate was coated with 30 ul of 2 ug/ml CD73 protein (ACRO, #CD3-H52H7-100 μg) solution and incubated overnight at 4° C. Then, the well plate was washed 3 times with PBST, blocked with 5% MILK/PBS at room temperature for 1 h, and then washed 3 times with PBST. The antigen-binding proteins 900567, 900725, 900726, 900727 and 900728 were all diluted to 10 μg/ml with 1% BSA in PBS solution (1% BSA/PBS) and then 4-fold diluted for 7 gradients. The diluted antigen-binding protein solutions were then added to the ELISA well plate, 30 ul per well, and incubated at room temperature for 30 min. After the incubation, the well plate was washed 3 times. Anti-human-IgG-Fc-HRP was added and incubated at room temperature for 50 min. After the incubation, the well plate was washed 3 times. The TMB solution was added. The reaction was then terminated with 2M HCl and the OD450 reading was checked.

Figure 2:
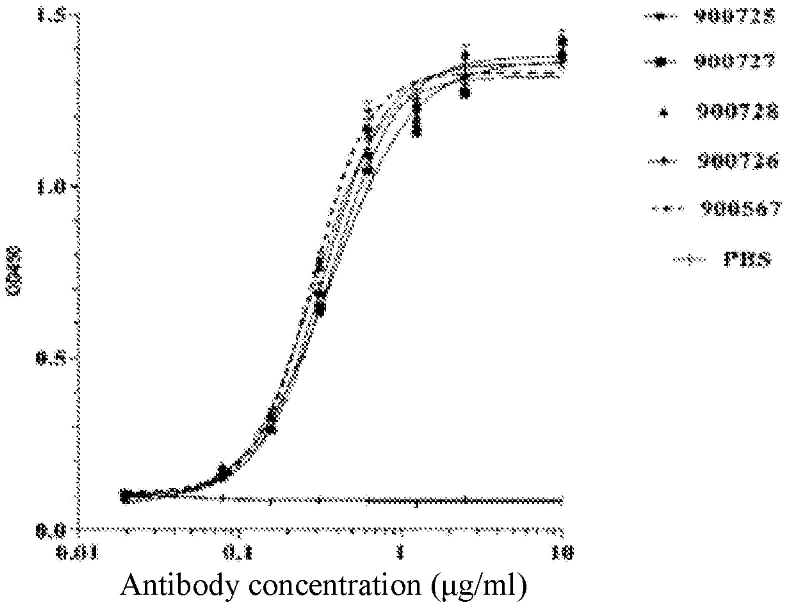
FIG. 2 shows the binding activity of the antigen-binding protein according to this application to a recombinant CD73.

The results of the binding activity of 900567, 900725, 900726, 900727 and 900728 to the recombinant CD73 protein (ACRO, #CD3-H52H7-100 μg) were shown in Table 5 and FIG. 2. The results showed that the antigen-binding proteins of this application were comparable in terms of affinity to the recombinant CD73 protein.

TABLE 5

Binding activity of 900567 and 900725-900728 to recombinant CD73 protein

| Antibody | 900567 | 900725 | 900726 | 900727 | 900728 |
|---|---|---|---|---|---|
| EC50 (ug/mL) | 0.2822 | 0.3273 | 0.361 | 0.3643 | 0.2901 |

Example 5 Testing on Inhibition Effect of Anti-CD73 Antigen-Binding Proteins Against Enzyme Activity of CD73

The antigen-binding proteins of this application were diluted to 30 μg/ml with PBS solution and then 5-fold diluted for 6 gradients. The suspension of cells (CHOK1-huCD73-3F4, Huabo Biopharm) expressing human CD73 during the logarithmic growth phase were incubated with medium to obtain $4\times10^5$/ml cell suspensions; and the cell suspensions were added, at 100 μL (about 40000 cells) per well, to a 96-well U-shaped plate and centrifuged (1500 rpm×5 min) to discard the supernatant. Then, the cells were resuspended with serially diluted antibodies, added at 100 ul per well, mixed well, and incubated at 37° C. for 20 min. After the incubation, the cell solutions were centrifuged (1500 rpm×5 min) to discard the supernatant, washed once with PBS at 200 ul/well, and then resuspended with 180 uM AMP at 100 ul/well, and incubated at 37° C. for 60 min. After the incubation, the cell solutions were centrifuged (1500 rpm×5 min). The supernatant was transferred to a 96-well black plate at 50 ul/well, and then add, at 50 ul/well, a prepared ATP and mixed well to react at 37° C. for 15 min. At last, CellTiter-Glo® Substrate was added to CellTiter-Glo® buffer, mixed well and equilibrated to room temperature, and then added, at 100 ul/well, to wells to be tested to react at room temperature for 10 min. After the reaction, Full wavelength detection was carried out. The percentage of enzyme activity was assessed as follows: Residual CD73 activity was calculated as: (CHOK1-huCD73-3F4 cell+Ab+ATP+AMP)−(ATP+AMP)/(CHOK1−huCD73−3F4 cell+ATP+AMP)−(ATP+AMP)*100.

Figure 3:
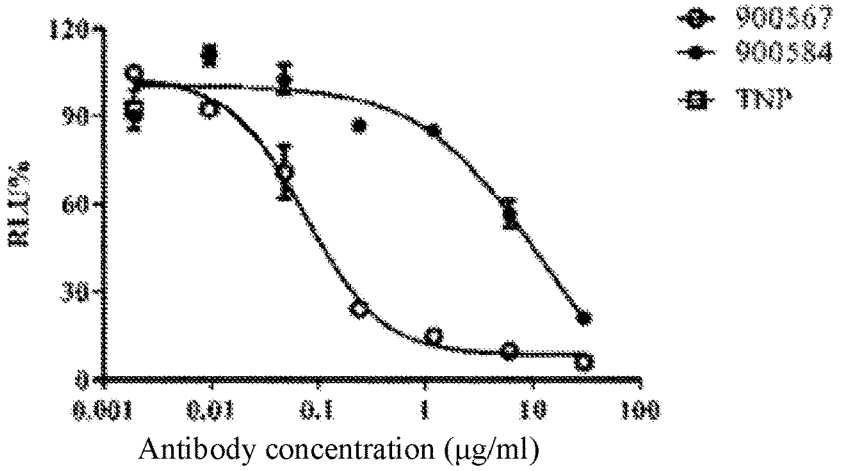
FIG. 3 shows results of a test on the enzyme activity inhibition of the antigen-binding protein according to this application against the CD73.
Figure 4:
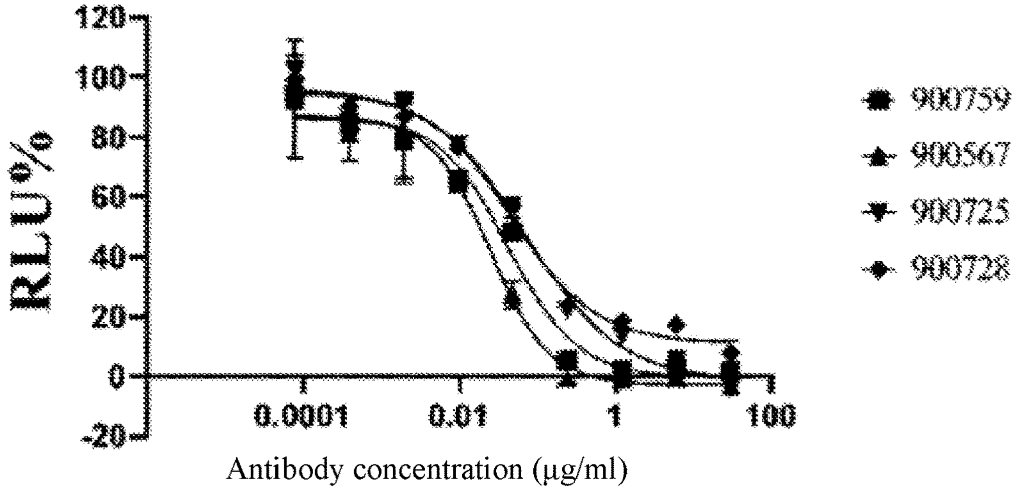
FIG. 4 shows results of a test on the enzyme inhibition activity of the antigen-binding protein according to this application against the CD73.

The results of the inhibition efficacy of 900567 and 900587 against the enzyme activity of cells (CHOK1-huCD73-3F4, Huabo Biopharm) with CD73 were shown in FIG. 3 and Table 6. The results of the inhibition effect of 900567, 900725, 900728, and Oleclumab negative control antibody (numbered as 900759 in this application and having a heavy chain sequence as set forth in SEQ ID NO: 39 and a light chain sequence as set forth in SEQ ID NO: 40) sourced from MedImmune Company against the enzyme activity of cells (CHOK1-huCD73-3F4, Huabo Biopharm) with CD73 were shown in FIG. 4 and Table 7. The results showed that the humanized antibodies 900725 and 900728 and the chimeric antibody 900567 had basically the same inhibition effect against the enzyme activity of CD73 on the cell membrane.

TABLE 6

Inhibition effect of 900567 and 900584 against the enzyme activity of CD73 on cell membrane

| Antibody | 900567 | 900584 |
|---|---|---|
| EC50 (ug/mL) | 0.07493 | 11.12 |

TABLE 7

Inhibition efficacy of 900759, 900567 and humanized antibodies 900725 and 900728 against the enzyme activity of CD73 on cell membrane

| Antibody | 900759 | 900567 | 900725 | 900728 |
|---|---|---|---|---|
| EC50 (ug/mL) | 0.04168 | 0.02502 | 0.06972 | 0.04669 |

Example 6 Testing on Binding Affinity of Anti-CD73 Antigen-Binding Proteins to Human CD73 Protein The binding kinetics of 900567, 900725, 900726, 900727 and 900728 to human CD73 protein (manufacturer: ACRO Biosystems, item No.: CD3-H52H7) was tested using Biacore (GE, model T200). In the tests, the assay buffer HBS-EP+ (pH 7.4) and the protein A chip (manufacturer: GE, item No.: 29-1275-56) were used.

The temperatures of a sample chamber and a flow path were set at 25° C., and the protein A chip respectively captured chimeric antibodies or humanized antibodies as ligands and immobilized at about 100 RU. Human CD73 protein was diluted with assay buffer to a series of concentrations of 50 nM, 25 nM, 12.5 nM, 6.25 nM, 3.12 nM, and 1.57 nM as analytes, and the assay buffer was used as the 0-concentration control. After association for 120 s at a flow rate of 30 μL/min, dissociation was carried out for 600 s. Regeneration was then carried out for 60 s with 10 mM Glycine (pH 1.5) at a flow rate of 50 μL/min to implement multi-cycle kinetic detection. A 1:1 binding model was selected for fitting analysis in a Fit local mode to acquire the association rate constant (ka), dissociation rate constant (kd) and dissociation equilibrium rate constant (KD). The fitting results were shown in Table 8. The results showed that the antigen-binding proteins of this application all were capable of binding to the human CD73 protein, and most of the antigen-binding proteins had no significant difference in binding affinity to the human CD73 protein.

TABLE 8

Testing results of binding affinity of anti-CD73 antigen-binding protein 900567 and its humanized antibodies to human CD73 protein

| Ligand | Analyte | ka (1/Ms) | kd (1/s) | KD (M) |
|---|---|---|---|---|
| 900567 | Human CD73 | 7.52E+05 | 4.90E−04 | 6.52E−10 |
| 900725 | Human CD73 | 6.26E+05 | 1.26E−04 | 2.01E−10 |
| 900726 | Human CD73 | 4.96E+05 | 1.24E−03 | 2.49E−9 |
| 900727 | Human CD73 | 6.26E+05 | 4.94E−04 | 7.89E−10 |
| 900728 | Human CD73 | 8.41E+05 | 3.17E−04 | 3.77E−10 |

Example 7 Testing on Binding Affinity of Anti-CD73 Antigen-Binding Proteins to CD73 Protein of Different Species (Human, Mouse, Rat, and Cynomolgus)

The binding kinetics of 900567, 900725, 900726, 900727 and 900728 to Human CD73 protein (manufacturer: ACRO Biosystems, item No.: CD3-H52H7), Mouse CD73/NT5E (manufacturer: ACRO Biosystems, item No.: CD3-M52H9), Rat CD73 (manufacturer: Novoprotein, item No.: CB16) and Cynomolgus CD73 (manufacturer: Novoprotein, item No.: CI21) was respectively tested using Biacore (GE, model T200). In the tests, the assay buffer HBS-EP+ (pH 7.4) and the protein A chip (manufacturer: GE, item No.: 29-1275-56) were used.

The temperatures of a sample chamber and a flow path were set at 25° C., and the protein A chip respectively captured antigen-binding proteins as ligands and immobilized at about 100 RU. The Human CD73 protein/Cynomolgus CD73/Rat CD73/Mouse CD73 was diluted with assay buffer to a series of concentrations of 50 nM, 25 nM, 12.5 nM, 6.25 nM, 3.12 nM, and 1.57 nM as analytes, and the assay buffer was used as the 0-concentration control. After association for 120 s at a flow rate of 30 μL/min, dissociation was carried out for 600 s. Regeneration was then carried out for 60 s with 10 mM Glycine (pH 1.5) at a flow rate of 50 μL/min to implement multi-cycle kinetic detection. A 1:1 binding model was selected for fitting analysis in a Fit local mode to acquire the association rate constant (ka), dissociation rate constant (kd) and dissociation equilibrium rate constant (KD). The fitting results were shown in Table 9. The results showed that the antigen-binding proteins of this application all were capable of binding to the Human CD73 protein and the Cynomolgus CD73 protein (manufacturer: Novoprotein, item No.: C121), and all the antigen-binding proteins were not capable of binding to the Mouse CD73/NT5E protein (manufacturer: ACRO Biosystems, item No.: CD3-M52H9).

TABLE 9

| Testing results of binding affinity of anti-CD73 antigen-binding protein 900567 and its humanized antigen-binding proteins to Cynomolgus CD73 protein | | | | |
|---|---|---|---|---|
| Ligand | Analyte | ka (1/Ms) | kd (1/s) | KD (M) |
| 900567 | Cynomolgus CD73 | 8.55E+05 | 6.06E−04 | 7.09E−10 |
| 900725 | Cynomolgus CD73 | 4.25E+05 | 1.56E−04 | 3.68E−10 |
| 900726 | Cynomolgus CD73 | 1.60E+06 | 3.20E−03 | 2.00E−9 |
| 900727 | Cynomolgus CD73 | 9.27E+05 | 7.40E−04 | 7.98E−10 |
| 900728 | Cynomolgus CD73 | 6.78E+05 | 3.81E−04 | 5.61E−10 |

Example 8 Testing on Capability of Anti-CD73 Antigen-Binding Proteins Inducing Endocytosis of CD73 on Cell Surface This example showed that the antigen-binding proteins of this application had a dual mechanism of action of blocking the enzymatic activity of CD73 and inducing endocytosis of CD73 on the cell surface. Specifically, CD73 series antigen-binding proteins were diluted with PBS solution to 1 μg/ml, and each concentration of the antigen-binding proteins was repeated in 2 wells. The suspension of Calu6 cells during the logarithmic growth phase were incubated to obtain $2\times10^5$/ml cell suspensions; and the cell suspensions were added, at 100 μL (about 20000 cells) per well, to a 96-well U-shaped plate and centrifuged (300 g×3 min) to discard the supernatant. The cells were then resuspended with diluted antigen-binding proteins at 100 μL/well, mixed well, and incubated at 4° C. for 30 min. After the incubation, the cell suspensions were centrifuged (300 g×3 min) to discard the supernatant. The cells were resuspended with 1% BSA, half of the cell suspensions were incubated at 37° C. for 5 h, and the other half were incubated at 4° C. for 5 h. After the incubation, the cells in wells corresponding to the incubation time were taken out and centrifuged at 300 g×3 min to discard the supernatant. PEanti-huIgGFc (1:200) was then added at 50 μL/well and mixed well to react at 4° C. for 30 min. After the incubation, the cells were washed twice (300 g×3 min), and then subjected to flow cytometry for fluorescence intensity.

Figure 5:
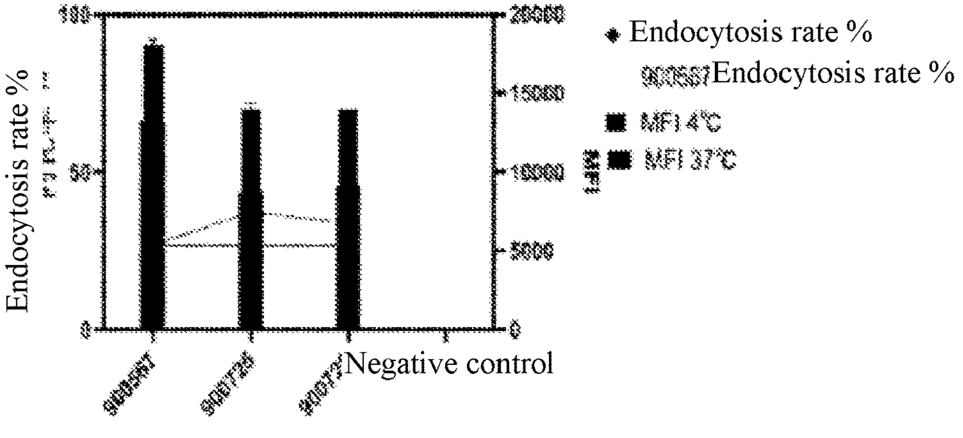
FIG. 5 shows results of a test on the ability of the antigen-binding protein according to this application to induce endocytosis of the CD73 on the cell surface.

The testing results of capability of anti-CD73 antigen-binding proteins inducing endocytosis of CD73 on the cell surface were shown in Table 10 and FIG. 5. The results showed that the anti-CD73 antigen-binding proteins 900567, 900725 and 900728 all were capable of inducing the endocytosis of CD73 on the cell surface.

TABLE 10

| Efficacy of anti-CD73 antigen-binding proteins inducing endocytosis of CD73 on cell surface | | | |
|---|---|---|---|
| Antibody | 900567 | 900725 | 900728 |
| Endocytosis rate (%) | 26.95 | 37.49 | 33.87 |

Example 9 Testing on Thermal Stability of Anti-CD73 Antigen-Binding Proteins

The melting temperature (Tm) and aggregation temperature (Tagg) of the anti-CD73 antigen-binding proteins 900567, 900725, 900726, 900727 and 900728 were tested by using a protein stability analyzer (UNcle, UNCHAINED LABS, US). The temperature heating ranges of Tm and Tagg were 25° C. to 95° C., and the heating rate was 0.3° C.

The results of thermal stability of the anti-CD73 antigen-binding proteins were shown in Table 11. The results showed that the Tm and T agg values of anti-CD73 antigen-binding proteins 900567, 900725, 900726, 900727 and 900728 were higher than 65° C., and the three humanized proteins 900725, 900726 and 900728 showed excellent thermal stability.

TABLE 11

| Testing results of thermal stability data (Tm and Tagg values) of anti-CD73 antigen binding proteins | | |
|---|---|---|
| Antibody | Tm value (° C.) | Tagg value (° C.) |
| 900567 | 69.4 | 66.3 |
| 900725 | 70.2 | 75.6 |
| 900726 | 70.2 | 74.1 |
| 900727 | 68.3 | 73.4 |
| 900728 | 70.5 | 74.1 |

Example 10 Testing on Non-Specific Adsorption Effect of Anti-CD73 Antigen-Binding Proteins The non-specific adsorption effect of antigen-binding proteins and non-target molecules were determined by using the SPR method.

Instruments and Equipment

| Name | Manufacturer | Model | No. |
|---|---|---|---|
| Biacore | GE | Biacore 8K | 1305 |

Reagents and Materials:

| Name | Manufacturer/ source | Item No. | Batch No. |
|---|---|---|---|
| Series Sensor Chip CM5 | GE | BR-1005-30 | 10253038 |
| Lysozyme solution from chicken egg | Sigma | L3790 | SLBM3565V |
| Trypsin inhibitor type 1-S from Glycine max | Sigma | T-2327 | SLBJ6832V |
| Polyclonal rabbit anti-lysozyme | ABcam | Ab391 | GR215714-19 |
| Anti-trypsin inhibitor antibody | LifeSpan Biosciences | LS-C76609 | 26978 |

The series sensor chip CM5 (GE, #BR-1005-30) was equilibrated at room temperature for 20-30 min and then loaded into the Biacore 8K (GE) instrument. Lysozyme solution (Sigma, #L3790) from egg and trypsin inhibitor type 1-S (Sigma, #T-2327) from Glycine max were immobilized onto the CM5 chip using an amino coupling kit (GE, #BR-1000-50). The injection buffer was HBS-EP (1×) (GE, #BR-1006-69) and four equilibration cycles were set up. The polyclonal rabbit anti-lysozyme (ABcam, Ab391), anti-trypsin inhibitor antibodies (LifeSpan Biosciences, #LS-C76609), chimeric antibodies and humanized antibodies were diluted with equilibration buffer to 1000 nM, and the flow rate was set at 5 μL/min and injection channels 1, 2 and 3, Flow Cell 1 and 2 were selected. The association time was 10 min and the dissociation time was 10 min. Regeneration was carried out, at a regeneration flow rate of 50 μL/min, with 0.85% phosphoric acid solution (ProteOn, 176-2260) for 60 s first and then with 50 mM sodium hydroxide solution for 30 s.

The PI of carboxymethyl dextran was 3.5, the PI of the trypsin inhibitor was 4.5, and the PI of lysozyme was 11.3. In the HBS-EP buffer solution with a pH of 7.4, carboxymethyl dextran and the trypsin inhibitor had strong negative charges, and lysozyme had strong positive charges. The testing results are shown in Table 12. The signal intensities of 900567, 900725, 900726, 900727 and 900728 were all less than or close to 20 U, so it could be considered that there was no non-specific electrostatic binding.

TABLE 12

Comparison of non-specific binding amount of samples

| Name | Carboxymethyl dextran (RU) | Inactive Carboxymethyl dextran (RU) | Lysozyme (RU) | Trypsin Inhibitor (RU) |
|---|---|---|---|---|
| Buffer | 16.1 | 18.6 | 16.9 | 13.9 |
| Polyclonal rabbit anti-lysozyme | 25.6 | 41.6 | 6504.1 | 37.3 |
| Anti-trypsin inhibitor | 37.1 | 41.0 | 51.6 | 9297.8 |
| 900567 | 11.0 | 13.3 | 15.8 | 12.8 |
| 900725 | 10.0 | 11.4 | 20.3 | 12.6 |
| 900726 | 14.1 | 15.8 | 17.7 | 15.4 |
| 900727 | 11.6 | 12.2 | 17.6 | 11.6 |
| 900728 | 11.3 | 13.6 | 20.2 | 13.5 |

Note: It is generally believed that after deducting the effect of the buffer, the interaction is weak and can be ignored if the response value is below 20 RU; if the response value exceeds 20 RU, it is considered to have an obvious interaction; if the response value exceeds 100 RU, it is considered to have a strong interaction.

Example 11 Testing on In Vivo Efficacy of Anti-CD73 Antigen-Binding Proteins on Tumor (1) CD73 humanized mice were used to establish an MDA-MB-231 triple-negative breast cancer animal model and test the efficacy of the tested antibody. First, CD73 humanized mice were inoculated with 100 μL of MDA-MB-231 (ATCC library) cells (2E6 cells) to establish CD73 humanized mouse MDA-MB-231 triple-negative breast cancer animal model. Tumor-forming mice were evenly divided into four experimental groups according to the tumor volume and body weight of the mice, 6 mice in each group, and administered by intraperitoneal injection, 2 times a week, a total of 6 times. The specific dosage regimen was shown in the table below. In the table, 900759 was an antibody derived from MedImmune's Oleclumab (MEDI 9447) antibody and the negative control 900201 was an antibody targeting TNP. The heavy chain amino acid sequence of 900201 was set forth in SEQ ID NO: 51 and the light chain amino acid sequence was set forth in SEQ ID NO: 52. The results showed that the antigen-binding proteins 900725 and 900728 of this application and the positive control antibody 900759 were all capable of effectively inhibiting the growth of MDA-MB-231 triple-negative breast cancer with comparable effects, but the negative control antibody 900201 was not capable of inhibiting tumor growth.

TABLE 13

Dosage regimen

| Group | Test substance | Number of animals | Route of administration | Dosing frequency a | Dosing times |
|---|---|---|---|---|---|
| G1 | 900201 | 6 | i.p. | BIW | 6 |
| G2 | 900759 | 6 | i.p. | BIW | 6 |
| G3 | 900725 | 6 | i.p. | BIW | 6 |
| G4 | 900728 | 6 | i.p. | BIW | 6 |

(2) NPG mice were used to establish an MDA-MB-231 triple-negative breast cancer animal model and test the efficacy of the tested antibody. The human breast cancer cells MDA-MB-231 used in this experiment were incubated in L-15 medium with 10% FBS in a CO2-free incubator at 37° C. Before the continuous incubation of cells for ten generations, $5.0\times10^6$ MDA-MB-231 cells was suspended in 100 μL of PBS, mixed with an equal volume of Matrigel, and inoculated on the right side of the back of NPG humanized mice near the armpit by subcutaneous injection with an inoculation volume of about 200 μL. The mice were anesthetized with 2-5% isoflurane before inoculation. On the day of inoculation, $1.0\times10^7$ PBMCs (100 μL) were injected via the tail vein. When the tumor grew to an average of about 50-80 $mm^3$, 18 tumor-bearing mice were randomly divided into three groups according to tumor volume and body weight, with 6 mice in each group. The mice were administered on the day of grouping, and the specific dosing regimen was shown in the table below. In the table, 900201 was negative control antibody and did not bind to CD73 antigen. Oleclumab is an anti-CD73 monoclonal antibody developed by AstraZeneca and currently in clinical phase II. The HC amino acid sequence of Oleclumab was set forth in SEQ ID NO: 53 and the LC amino acid sequence of Oleclumab was set forth in SEQ ID NO: 54.

Figure 6:
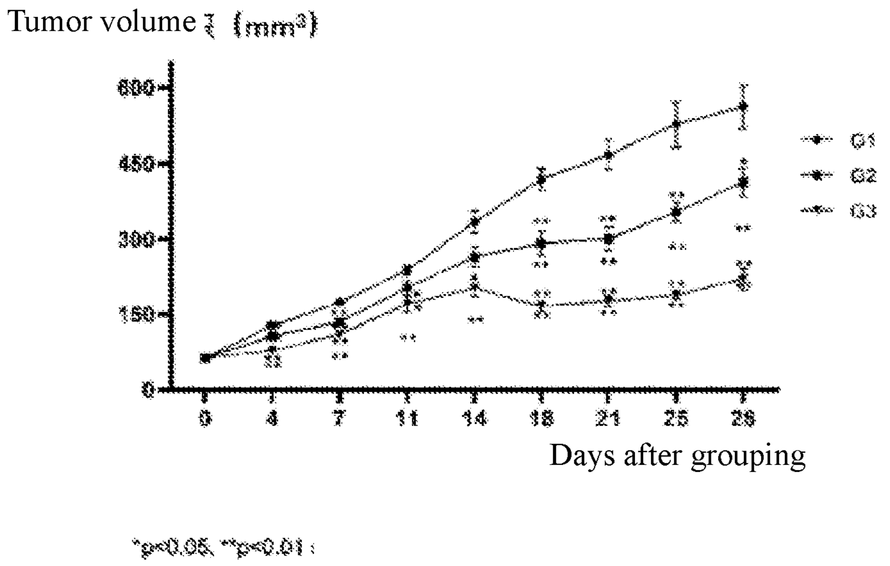
FIG. 6 shows the treatment effect of the antigen-binding protein according to this application on tumors in vivo.

The results, as shown in Table 14 and FIG. 6 below, indicated that oleclumab and 900725 could significantly inhibit the growth of MDA-MB-211 triple-negative breast cancer, and the tumor inhibition effect of 900725 was better than that of the positive control oleculumab, while the negative control antibody 900201 could not inhibit tumor growth.

TABLE 14

Dosage regimen

| Group | Test substance | Number of animals | Administration dose (mg/kg) | Route of administration | Dosing frequency a | Dosing times |
|---|---|---|---|---|---|---|
| G1 | 900201 | 6 | 5 | i.p. | BIW | 8 |
| G2 | oleclumab | 6 | 5 | i.p. | BIW | 8 |
| G3 | 900725 | 6 | 5 | i.p. | BIW | 8 |

Example 12 Testing on In Vivo Efficacy of Anti-CD73 Antigen-Binding Proteins on Pancreatic Cancer NPG mice were used to establish a BxPC-3 pancreatic cancer animal model and test the efficacy of the tested antibody. Human pancreatic cancer cells BxPC-3 used in this experiment were incubated in RPMI-1640 medium with 10% FBS in an incubator with 5% $CO_2$ at 37° C. Before the continuous incubation of cells for ten generations, 1004, of PBS containing $1\times10^7$ MDA-MB-231 cells was mixed with an equal volume of Matrigel, and inoculated on the right side of the back of 18 NPG mice near the armpit by subcutaneous injection with an inoculation volume of about 200 μL. The mice were anesthetized with 2-5% isoflurane before inoculation. On the day of inoculation, $1.0\times10^7$ PBMCs (100 μL) were injected via the tail vein. When the tumor grew to an average of about 50-80 $mm^3$, 18 tumor-bearing mice were randomly divided into three groups according to tumor volume and body weight, with 6 mice in each group. The mice were administered on the day of grouping, and the specific dosing regimen was shown in the table 15 below. In the table, 900543 was a negative control antibody (900543 is an ADCC knockout type of 900201 with a heavy chain amino acid sequence as set forth in SEQ ID NO: 55) did not bind to CD73 antigen. Oleclumab is an anti-CD73 monoclonal antibody developed by AstraZeneca and currently in clinical phase II.

Figure 7:
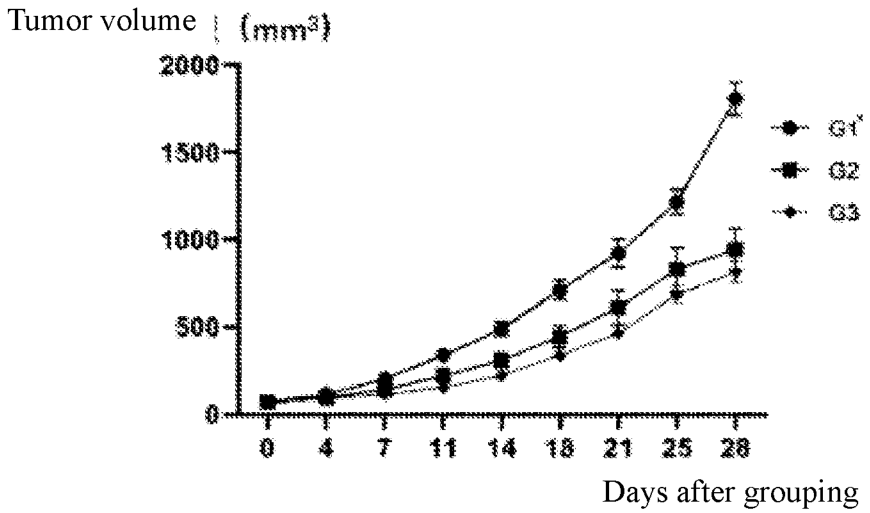
FIG. 7 shows the treatment effect of the antigen-binding protein according to this application on tumors in vivo.

The results, as shown in FIG. 7 below, indicated that oleclumab and 900725 could significantly inhibit the growth of BxPC-3 pancreatic cancer, and the tumor inhibition effect of 900725 was better than that of the positive control oleculumab, while the negative control antibody 900543 could not inhibit tumor growth.

TABLE 15

| Dosage regimen | | | | | | |
|---|---|---|---|---|---|---|
| Group | Test substance | Number of animals | Administration dose (mg/kg) | Route of administration | Dosing frequency a | Dosing times |
| G1' | 900543 | 6 | 5 | i.p. | BIW | 8 |
| G2 | oleclumab | 6 | 5 | i.p. | BIW | 8 |
| G3 | 900725 | 6 | 5 | i.p. | BIW | 8 |

All documents mentioned in this application are incorporated by reference in this application as if each document were individually incorporated by reference. In addition, it should be understood that after reading the above teaching content of this application, those skilled in the art can make various changes or modifications to this application, and these equivalent forms also fall within the scope defined by the appended claims of this application.

What is claimed is:

1. An isolated antigen-binding protein, which is capable of specifically binding to a CD73 or a functionally active fragment thereof, comprising HCDR1, HCDR2, HCDR3, LCDR1, LCDR2, and LCDR3, wherein said HCDR1 comprises an amino acid sequence as set forth in SEQ ID NO: 3, said HCDR2 comprises an amino acid sequence as set forth in SEQ ID NO: 2, said HCDR3 comprises an amino acid sequence as set forth in SEQ ID NO: 1, said LCDR1 comprises an amino acid sequence as set forth in SEQ ID NO: 6, said LCDR2 comprises an amino acid sequence as set forth in SEQ ID NO: 5, and said LCDR3 comprises an amino acid sequence as set forth in SEQ ID NO: 4.

2. The isolated antigen-binding protein of claim 1, comprising any set of amino acid sequences selected from the group consisting of:

1) said VH comprises an amino acid sequence as set forth in SEQ ID NO: 28 and said VL comprises an amino acid sequence as set forth in SEQ ID NO: 29;
2) Said VH comprises an amino acid sequence as set forth in SEQ ID NO: 30 and said VL comprises an amino acid sequence as set forth in SEQ ID NO: 31;
3) said VH comprises an amino acid sequence as set forth in SEQ ID NO: 30 and said VL comprises an amino acid sequence as set forth in SEQ ID NO: 33;
4) said VH comprises an amino acid sequence as set forth in SEQ ID NO: 32 and said VL comprises an amino acid sequence as set forth in SEQ ID NO: 31; and
5) said VH comprises an amino acid sequence as set forth in SEQ ID NO: 34 and said VL comprises an amino acid sequence as set forth in SEQ ID NO: 33.

3. The isolated antigen-binding protein of claim 1, comprising an antibody heavy-chain constant region and an antibody light-chain constant region; wherein said antibody heavy-chain constant region is derived from a human IgG heavy-chain constant region, wherein said antibody light-chain constant region is derived from a human Igκ constant region.

4. A polypeptide molecule, comprising the isolated antigen-binding protein of claim 1.

5. A nucleic acid molecule, encoding the isolated antigen-binding protein according of claim 1.

6. A vector, comprising the nucleic acid molecule according to claim 5.

7. An immunoconjugate, comprising the isolated antigen-binding protein of claim 1.

8. A cell, comprising the nucleic acid molecule of claim 5.

9. A pharmaceutical composition, comprising the isolated antigen-binding protein of claim 1, and a pharmaceutically acceptable carrier.

10. A method of treating a disease and/or disorder, comprising administering to a subject in need thereof the isolated antigen-binding protein of claim 1, wherein said disease and/or disorder is mediated by the CD73.

11. A method for detecting CD73 in a sample, comprising administering the isolated antigen binding protein of claim 1.

* * * * *